(12) United States Patent
Eldardiry et al.

(10) Patent No.: US 10,610,144 B2
(45) Date of Patent: Apr. 7, 2020

(54) INTERACTIVE REMOTE PATIENT MONITORING AND CONDITION MANAGEMENT INTERVENTION SYSTEM

(71) Applicant: Palo Alto Research Center Incorporated, Palo Alto, CA (US)

(72) Inventors: Hoda M. A. Eldardiry, San Carlos, CA (US); Jonathan Rubin, Mountain View, CA (US); Rui Abreu, Sunnyvale, CA (US); Shane P. Ahern, Foster City, CA (US); Daniel G. Bobrow, Palo Alto, CA (US); David Garcia, Stanford, CA (US); Honglu Du, Santa Clara, CA (US); Ashish Pattekar, Cupertino, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 702 days.

(21) Appl. No.: 14/830,533

(22) Filed: Aug. 19, 2015

(65) Prior Publication Data

US 2017/0049374 A1    Feb. 23, 2017

(51) Int. Cl.
*A61B 5/16* (2006.01)
*A61B 5/0205* (2006.01)
(Continued)

(52) U.S. Cl.
CPC .......... *A61B 5/165* (2013.01); *A61B 5/02055* (2013.01); *A61B 5/08* (2013.01); *A61B 5/14552* (2013.01)

(58) Field of Classification Search
CPC ... A61B 5/02055; A61B 5/08; A61B 5/14552; G06F 19/345; G06F 19/3418; G06F 19/3431
See application file for complete search history.

(56) References Cited

U.S. PATENT DOCUMENTS 817,441 A    4/1906  Niesz
4,309,569 A  1/1982  Merkle
(Continued)

FOREIGN PATENT DOCUMENTS

DE    1720277 A1    6/1967
DE    19620817 A1   11/1997
(Continued)

OTHER PUBLICATIONS

Healthwise staff, www.cardiosmart.org/healthwaise/rlxs/k/rlxsk, "Stress Management, Topic Overview", Apr. 20, 2011, Healthwise, CardioSmart American College of Cardiology (Year: 2011).*
(Continued)

*Primary Examiner* — Evangeline Barr
(74) *Attorney, Agent, or Firm* — Shun Yao; Park, Vaughan, Fleming & Dowler LLP

(57) ABSTRACT

A method and system for generating a personalized health management recommendation for a user. During operation, the system obtains first physiological data generated by a wearable device worn by the user that indicates a physiological condition of the user. The system then generates a prediction model for the user based on the first physiological data. Next, the system obtains real-time physiological data generated by the wearable device. The system may generate a prediction by analyzing the real-time physiological data to determine whether the user's physiological condition exceeds a threshold parameter according to the prediction model. Upon determining that the threshold parameter has been exceeded, the system may select a recommendation and send the recommendation message to the user's mobile device.

19 Claims, 19 Drawing Sheets

(51) Int. Cl.
*A61B 5/08* (2006.01)
*A61B 5/1455* (2006.01)

(56) References Cited

U.S. PATENT DOCUMENTS

| | | |
|---|---|---|
| 4,921,898 A | 5/1990 | Lenney |
| 5,070,134 A | 12/1991 | Oyamada |
| 5,110,856 A | 5/1992 | Oyamada |
| 5,506,844 A | 4/1996 | Rao |
| 5,629,370 A | 5/1997 | Freidzon |
| 5,870,605 A | 2/1999 | Bracho |
| 6,052,683 A | 4/2000 | Irwin |
| 6,091,724 A | 7/2000 | Chandra |
| 6,173,364 B1 | 1/2001 | Zenchelsky |
| 6,226,618 B1 | 5/2001 | Downs |
| 6,233,646 B1 | 5/2001 | Hahm |
| 6,332,158 B1 | 12/2001 | Risley |
| 6,366,988 B1 | 4/2002 | Skiba |
| 6,574,377 B1 | 6/2003 | Cahill |
| 6,654,792 B1 | 11/2003 | Verma |
| 6,667,957 B1 | 12/2003 | Corson |
| 6,681,220 B1 | 1/2004 | Kaplan |
| 6,681,326 B2 | 1/2004 | Son |
| 6,769,066 B1 | 7/2004 | Botros |
| 6,772,333 B1 | 8/2004 | Brendel |
| 6,862,280 B1 | 3/2005 | Bertagna |
| 6,901,452 B1 | 5/2005 | Bertagna |
| 6,917,985 B2 | 7/2005 | Madruga |
| 6,968,393 B1 | 11/2005 | Chen |
| 6,981,029 B1 | 12/2005 | Menditto |
| 7,013,389 B1 | 3/2006 | Srivastava |
| 7,031,308 B2 | 4/2006 | Garcia-Luna-Aceves |
| 7,061,877 B1 | 6/2006 | Gummalla |
| 7,206,860 B2 | 4/2007 | Murakami |
| 7,257,837 B2 | 8/2007 | Xu |
| 7,287,275 B2 | 10/2007 | Moskowitz |
| 7,315,541 B1 | 1/2008 | Housel |
| 7,339,929 B2 | 3/2008 | Zelig |
| 7,350,229 B1 | 3/2008 | Lander |
| 7,382,787 B1 | 6/2008 | Barnes |
| 7,444,251 B2 | 10/2008 | Nikovski |
| 7,466,703 B1 | 12/2008 | Arunachalam |
| 7,472,422 B1 | 12/2008 | Agbabian |
| 7,496,668 B2 | 2/2009 | Hawkinson |
| 7,509,425 B1 | 3/2009 | Rosenberg |
| 7,523,016 B1 | 4/2009 | Surdulescu |
| 7,543,064 B2 | 6/2009 | Juncker |
| 7,552,233 B2 | 6/2009 | Raju |
| 7,555,482 B2 | 6/2009 | Korkus |
| 7,555,563 B2 | 6/2009 | Ott |
| 7,567,547 B2 | 7/2009 | Mosko |
| 7,567,946 B2 | 7/2009 | Andreoli |
| 7,580,971 B1 | 8/2009 | Gollapudi |
| 7,623,535 B2 | 11/2009 | Guichard |
| 7,647,507 B1 | 1/2010 | Feng |
| 7,660,324 B2 | 2/2010 | Oguchi |
| 7,685,290 B2 | 3/2010 | Satapati |
| 7,698,463 B2 | 4/2010 | Ogier |
| 7,769,887 B1 | 8/2010 | Bhattacharyya |
| 7,779,467 B2 | 8/2010 | Choi |
| 7,801,177 B2 | 9/2010 | Luss |
| 7,816,441 B2 | 10/2010 | Elizalde |
| 7,831,733 B2 | 11/2010 | Sultan |
| 7,908,337 B2 | 3/2011 | Garcia-Luna-Aceves |
| 7,924,837 B1 | 4/2011 | Shabtay |
| 7,953,885 B1 | 5/2011 | Devireddy |
| 8,000,267 B2 | 8/2011 | Solis |
| 8,010,691 B2 | 8/2011 | Kollmansberger |
| 8,074,289 B1 | 12/2011 | Carpentier |
| 8,117,441 B2 | 2/2012 | Kurien |
| 8,160,069 B2 | 4/2012 | Jacobson |
| 8,204,060 B2 | 6/2012 | Jacobson |
| 8,214,364 B2 | 7/2012 | Bigus |
| 8,224,985 B2 | 7/2012 | Takeda |
| 8,225,057 B1 | 7/2012 | Zheng |
| 8,271,578 B2 | 9/2012 | Sheffi |
| 8,312,064 B1 | 11/2012 | Gauvin |
| 8,386,622 B2 | 2/2013 | Jacobson |
| 8,467,297 B2 | 6/2013 | Liu |
| 8,553,562 B2 | 10/2013 | Allan |
| 8,572,214 B2 | 10/2013 | Garcia-Luna-Aceves |
| 8,654,649 B2 | 2/2014 | Vasseur |
| 8,665,757 B2 | 3/2014 | Kling |
| 8,667,172 B2 | 3/2014 | Ravindran |
| 8,688,619 B1 | 4/2014 | Ezick |
| 8,699,350 B1 | 4/2014 | Kumar |
| 8,750,820 B2 | 6/2014 | Allan |
| 8,761,022 B2 | 6/2014 | Chiabaut |
| 8,762,477 B2 | 6/2014 | Xie |
| 8,762,570 B2 | 6/2014 | Qian |
| 8,762,707 B2 | 6/2014 | Killian |
| 8,767,627 B2 | 7/2014 | Ezure |
| 8,817,594 B2 | 8/2014 | Gero |
| 8,826,381 B2 | 9/2014 | Kim |
| 8,832,302 B1 | 9/2014 | Bradford |
| 8,836,536 B2 | 9/2014 | Marwah |
| 8,862,774 B2 | 10/2014 | Vasseur |
| 8,903,756 B2 | 12/2014 | Zhao |
| 8,937,865 B1 | 1/2015 | Kumar |
| 9,071,498 B2 | 6/2015 | Beser |
| 9,112,895 B1 | 8/2015 | Lin |
| 2002/0010795 A1 | 1/2002 | Brown |
| 2002/0048269 A1 | 4/2002 | Hong |
| 2002/0054593 A1 | 5/2002 | Morohashi |
| 2002/0077988 A1 | 6/2002 | Sasaki |
| 2002/0078066 A1 | 6/2002 | Robinson |
| 2002/0138551 A1 | 9/2002 | Erickson |
| 2002/0176404 A1 | 11/2002 | Girard |
| 2002/0188605 A1 | 12/2002 | Adya |
| 2002/0199014 A1 | 12/2002 | Yang |
| 2003/0046437 A1 | 3/2003 | Eytchison |
| 2003/0048793 A1 | 3/2003 | Pochon |
| 2003/0051100 A1 | 3/2003 | Patel |
| 2003/0074472 A1 | 4/2003 | Lucco |
| 2003/0097447 A1 | 5/2003 | Johnston |
| 2003/0140257 A1 | 7/2003 | Paterka |
| 2004/0024879 A1 | 2/2004 | Dingman |
| 2004/0030602 A1 | 2/2004 | Rosenquist |
| 2004/0073715 A1 | 4/2004 | Folkes |
| 2004/0139230 A1 | 7/2004 | Kim |
| 2004/0221047 A1 | 11/2004 | Grover |
| 2004/0225627 A1 | 11/2004 | Botros |
| 2004/0252683 A1 | 12/2004 | Kennedy |
| 2005/0003832 A1 | 1/2005 | Osafune |
| 2005/0028156 A1 | 2/2005 | Hammond |
| 2005/0043060 A1 | 2/2005 | Brandenberg |
| 2005/0050211 A1 | 3/2005 | Kaul |
| 2005/0074001 A1 | 4/2005 | Mattes |
| 2005/0149508 A1 | 7/2005 | Deshpande |
| 2005/0159823 A1 | 7/2005 | Hayes |
| 2005/0198351 A1 | 9/2005 | Nog |
| 2005/0249196 A1 | 11/2005 | Ansari |
| 2005/0259637 A1 | 11/2005 | Chu |
| 2005/0262217 A1 | 11/2005 | Nonaka |
| 2005/0289222 A1 | 12/2005 | Sahim |
| 2006/0010249 A1 | 1/2006 | Sabesan |
| 2006/0029102 A1 | 2/2006 | Abe |
| 2006/0039379 A1 | 2/2006 | Abe |
| 2006/0051055 A1 | 3/2006 | Ohkawa |
| 2006/0072523 A1 | 4/2006 | Richardson |
| 2006/0099973 A1 | 5/2006 | Nair |
| 2006/0129514 A1 | 6/2006 | Watanabe |
| 2006/0133343 A1 | 6/2006 | Huang |
| 2006/0167825 A1* | 7/2006 | Sayal ................. G06N 5/022 706/45 |
| 2006/0173831 A1 | 8/2006 | Basso |
| 2006/0193295 A1 | 8/2006 | White |
| 2006/0206445 A1 | 9/2006 | Andreoli |
| 2006/0215684 A1 | 9/2006 | Capone |
| 2006/0223504 A1 | 10/2006 | Ishak |
| 2006/0256767 A1 | 11/2006 | Suzuki |
| 2006/0268792 A1 | 11/2006 | Belcea |
| 2007/0019619 A1 | 1/2007 | Foster |
| 2007/0073888 A1 | 3/2007 | Madhok |

(56) References Cited

U.S. PATENT DOCUMENTS

| | | |
|---|---|---|
| 2007/0094265 A1 | 4/2007 | Korkus |
| 2007/0112880 A1 | 5/2007 | Yang |
| 2007/0124412 A1 | 5/2007 | Narayanaswami |
| 2007/0127457 A1 | 6/2007 | Mirtorabi |
| 2007/0160062 A1 | 7/2007 | Morishita |
| 2007/0162394 A1 | 7/2007 | Zager |
| 2007/0189284 A1 | 8/2007 | Kecskemeti |
| 2007/0195765 A1 | 8/2007 | Heissenbuttel |
| 2007/0204011 A1 | 8/2007 | Shaver |
| 2007/0209067 A1 | 9/2007 | Fogel |
| 2007/0239892 A1 | 10/2007 | Ott |
| 2007/0240207 A1 | 10/2007 | Belakhdar |
| 2007/0245034 A1 | 10/2007 | Retana |
| 2007/0253418 A1 | 11/2007 | Shiri |
| 2007/0255699 A1 | 11/2007 | Sreenivas |
| 2007/0255781 A1 | 11/2007 | Li |
| 2007/0274504 A1 | 11/2007 | Maes |
| 2007/0276907 A1 | 11/2007 | Maes |
| 2007/0294187 A1 | 12/2007 | Scherrer |
| 2008/0005056 A1 | 1/2008 | Stelzig |
| 2008/0010366 A1 | 1/2008 | Duggan |
| 2008/0037420 A1 | 2/2008 | Tang |
| 2008/0043989 A1 | 2/2008 | Furutono |
| 2008/0046340 A1 | 2/2008 | Brown |
| 2008/0059631 A1 | 3/2008 | Bergstrom |
| 2008/0080440 A1 | 4/2008 | Yarvis |
| 2008/0101357 A1 | 5/2008 | Iovanna |
| 2008/0107034 A1 | 5/2008 | Jetcheva |
| 2008/0123862 A1 | 5/2008 | Rowley |
| 2008/0133583 A1 | 6/2008 | Artan |
| 2008/0133755 A1 | 6/2008 | Pollack |
| 2008/0151755 A1 | 6/2008 | Nishioka |
| 2008/0159271 A1 | 7/2008 | Kutt |
| 2008/0186901 A1 | 8/2008 | Itagaki |
| 2008/0200153 A1 | 8/2008 | Fitzpatrick |
| 2008/0215669 A1 | 9/2008 | Gaddy |
| 2008/0216086 A1 | 9/2008 | Tanaka |
| 2008/0243992 A1 | 10/2008 | Jardetzky |
| 2008/0256359 A1 | 10/2008 | Kahn |
| 2008/0270618 A1 | 10/2008 | Rosenberg |
| 2008/0271143 A1 | 10/2008 | Stephens |
| 2008/0287142 A1 | 11/2008 | Keighran |
| 2008/0288580 A1 | 11/2008 | Wang |
| 2008/0320148 A1 | 12/2008 | Capuozzo |
| 2009/0006659 A1 | 1/2009 | Collins |
| 2009/0013324 A1 | 1/2009 | Gobara |
| 2009/0022154 A1 | 1/2009 | Kiribe |
| 2009/0024641 A1 | 1/2009 | Quigley |
| 2009/0030978 A1 | 1/2009 | Johnson |
| 2009/0037763 A1 | 2/2009 | Adhya |
| 2009/0052660 A1 | 2/2009 | Chen |
| 2009/0067429 A1 | 3/2009 | Nagai |
| 2009/0077184 A1 | 3/2009 | Brewer |
| 2009/0092043 A1 | 4/2009 | Lapuh |
| 2009/0097631 A1 | 4/2009 | Gisby |
| 2009/0103515 A1 | 4/2009 | Pointer |
| 2009/0113068 A1 | 4/2009 | Fujihira |
| 2009/0144300 A1 | 6/2009 | Chatley |
| 2009/0157887 A1 | 6/2009 | Froment |
| 2009/0185745 A1 | 7/2009 | Momosaki |
| 2009/0193101 A1 | 7/2009 | Munetsugu |
| 2009/0222344 A1 | 9/2009 | Greene |
| 2009/0228593 A1 | 9/2009 | Takeda |
| 2009/0254572 A1 | 10/2009 | Redlich |
| 2009/0268905 A1 | 10/2009 | Matsushima |
| 2009/0285209 A1 | 11/2009 | Stewart |
| 2009/0287835 A1 | 11/2009 | Jacobson |
| 2009/0288163 A1 | 11/2009 | Jacobson |
| 2009/0292743 A1 | 11/2009 | Bigus |
| 2009/0293121 A1 | 11/2009 | Bigus |
| 2009/0300079 A1 | 12/2009 | Shitomi |
| 2009/0300407 A1 | 12/2009 | Kamath |
| 2009/0307333 A1 | 12/2009 | Welingkar |
| 2009/0323632 A1 | 12/2009 | Nix |
| 2010/0005061 A1 | 1/2010 | Basco |
| 2010/0027539 A1 | 2/2010 | Beverly |
| 2010/0046546 A1 | 2/2010 | Ram |
| 2010/0057929 A1 | 3/2010 | Merat |
| 2010/0088370 A1 | 4/2010 | Wu |
| 2010/0094767 A1 | 4/2010 | Miltonberger |
| 2010/0098093 A1 | 4/2010 | Ejzak |
| 2010/0100465 A1 | 4/2010 | Cooke |
| 2010/0103870 A1 | 4/2010 | Garcia-Luna-Aceves |
| 2010/0124191 A1 | 5/2010 | Vos |
| 2010/0125911 A1 | 5/2010 | Bhaskaran |
| 2010/0131660 A1 | 5/2010 | Dec |
| 2010/0150155 A1 | 6/2010 | Napierala |
| 2010/0165976 A1 | 7/2010 | Khan |
| 2010/0169478 A1 | 7/2010 | Saha |
| 2010/0169503 A1 | 7/2010 | Kollmansberger |
| 2010/0180332 A1 | 7/2010 | Ben-Yochanan |
| 2010/0182995 A1 | 7/2010 | Hwang |
| 2010/0185753 A1 | 7/2010 | Liu |
| 2010/0195653 A1 | 8/2010 | Jacobson |
| 2010/0195654 A1 | 8/2010 | Jacobson |
| 2010/0195655 A1 | 8/2010 | Jacobson |
| 2010/0217874 A1 | 8/2010 | Anantharaman |
| 2010/0232402 A1 | 9/2010 | Przybysz |
| 2010/0232439 A1 | 9/2010 | Dham |
| 2010/0235516 A1 | 9/2010 | Nakamura |
| 2010/0246549 A1 | 9/2010 | Zhang |
| 2010/0250497 A1 | 9/2010 | Redlich |
| 2010/0250939 A1 | 9/2010 | Adams |
| 2010/0268782 A1 | 10/2010 | Zombek |
| 2010/0272107 A1 | 10/2010 | Papp |
| 2010/0284309 A1 | 11/2010 | Allan |
| 2010/0284404 A1 | 11/2010 | Gopinath |
| 2010/0293293 A1 | 11/2010 | Beser |
| 2010/0322249 A1 | 12/2010 | Thathapudi |
| 2011/0013637 A1 | 1/2011 | Xue |
| 2011/0022812 A1 | 1/2011 | vanderLinden |
| 2011/0055392 A1 | 3/2011 | Shen |
| 2011/0055921 A1 | 3/2011 | Narayanaswamy |
| 2011/0090908 A1 | 4/2011 | Jacobson |
| 2011/0106755 A1 | 5/2011 | Hao |
| 2011/0145597 A1 | 6/2011 | Yamaguchi |
| 2011/0145858 A1 | 6/2011 | Philpott et al. |
| 2011/0153840 A1 | 6/2011 | Narayana |
| 2011/0161408 A1 | 6/2011 | Kim |
| 2011/0202609 A1 | 8/2011 | Chaturvedi |
| 2011/0231578 A1 | 9/2011 | Nagappan |
| 2011/0239256 A1 | 9/2011 | Gholmieh |
| 2011/0245633 A1* | 10/2011 | Goldberg ............... A61B 5/681 600/301 |
| 2011/0258049 A1 | 10/2011 | Ramer |
| 2011/0264824 A1 | 10/2011 | Venkata Subramanian |
| 2011/0265174 A1 | 10/2011 | Thornton |
| 2011/0271007 A1 | 11/2011 | Wang |
| 2011/0286457 A1 | 11/2011 | Ee |
| 2011/0286459 A1 | 11/2011 | Rembarz |
| 2011/0295783 A1 | 12/2011 | Zhao |
| 2011/0299454 A1 | 12/2011 | Krishnaswamy |
| 2012/0011170 A1 | 1/2012 | Elad |
| 2012/0011551 A1 | 1/2012 | Levy |
| 2012/0036180 A1 | 2/2012 | Thornton |
| 2012/0047361 A1 | 2/2012 | Erdmann |
| 2012/0066727 A1 | 3/2012 | Nozoe |
| 2012/0106339 A1 | 5/2012 | Mishra |
| 2012/0114313 A1 | 5/2012 | Phillips |
| 2012/0120803 A1 | 5/2012 | Farkas |
| 2012/0136676 A1 | 5/2012 | Goodall |
| 2012/0136936 A1 | 5/2012 | Quintuna |
| 2012/0136945 A1 | 5/2012 | Lee |
| 2012/0137367 A1 | 5/2012 | Dupont |
| 2012/0141093 A1 | 6/2012 | Yamaguchi |
| 2012/0155464 A1 | 6/2012 | Kim |
| 2012/0158973 A1 | 6/2012 | Jacobson |
| 2012/0163373 A1 | 6/2012 | Lo |
| 2012/0179653 A1 | 7/2012 | Araki |
| 2012/0197690 A1 | 8/2012 | Agulnek |
| 2012/0198048 A1 | 8/2012 | Ioffe |
| 2012/0221150 A1 | 8/2012 | Arensmeier |
| 2012/0224487 A1 | 9/2012 | Hui |
| 2012/0257500 A1 | 10/2012 | Lynch |

(56) References Cited

U.S. PATENT DOCUMENTS

| | | |
|---|---|---|
| 2012/0284791 A1 | 11/2012 | Miller |
| 2012/0290669 A1 | 11/2012 | Parks |
| 2012/0290919 A1 | 11/2012 | Melnyk |
| 2012/0291102 A1 | 11/2012 | Cohen |
| 2012/0314580 A1 | 12/2012 | Hong |
| 2012/0317307 A1 | 12/2012 | Ravindran |
| 2012/0331112 A1 | 12/2012 | Chatani |
| 2013/0041982 A1 | 2/2013 | Shi |
| 2013/0051392 A1 | 2/2013 | Filsfils |
| 2013/0060962 A1 | 3/2013 | Wang |
| 2013/0073552 A1 | 3/2013 | Rangwala |
| 2013/0074155 A1 | 3/2013 | Huh |
| 2013/0091539 A1 | 4/2013 | Khurana |
| 2013/0110987 A1 | 5/2013 | Kim |
| 2013/0111063 A1 | 5/2013 | Lee |
| 2013/0151584 A1 | 6/2013 | Westphal |
| 2013/0163426 A1 | 6/2013 | Beliveau |
| 2013/0166668 A1 | 6/2013 | Byun |
| 2013/0173822 A1 | 7/2013 | Hong |
| 2013/0182568 A1 | 7/2013 | Lee |
| 2013/0185406 A1 | 7/2013 | Choi |
| 2013/0197698 A1 | 8/2013 | Shah |
| 2013/0198119 A1 | 8/2013 | Eberhardt, III |
| 2013/0219038 A1 | 8/2013 | Lee |
| 2013/0219081 A1 | 8/2013 | Qian |
| 2013/0219478 A1 | 8/2013 | Mahamuni |
| 2013/0223237 A1 | 8/2013 | Hui |
| 2013/0227166 A1 | 8/2013 | Ravindran |
| 2013/0242996 A1 | 9/2013 | Varvello |
| 2013/0250809 A1 | 9/2013 | Hui |
| 2013/0282854 A1 | 10/2013 | Jang |
| 2013/0282860 A1 | 10/2013 | Zhang |
| 2013/0282920 A1 | 10/2013 | Zhang |
| 2013/0304937 A1 | 11/2013 | Lee |
| 2013/0329696 A1 | 12/2013 | Xu |
| 2013/0336323 A1 | 12/2013 | Srinivasan |
| 2013/0343408 A1 | 12/2013 | Cook |
| 2014/0003232 A1 | 1/2014 | Guichard |
| 2014/0006565 A1 | 1/2014 | Muscariello |
| 2014/0029445 A1 | 1/2014 | Hui |
| 2014/0032714 A1 | 1/2014 | Liu |
| 2014/0040505 A1 | 2/2014 | Barton |
| 2014/0074730 A1 | 3/2014 | Arensmeier |
| 2014/0075567 A1 | 3/2014 | Raleigh |
| 2014/0082135 A1 | 3/2014 | Jung |
| 2014/0089454 A1 | 3/2014 | Jeon |
| 2014/0096249 A1 | 4/2014 | Dupont |
| 2014/0129736 A1 | 5/2014 | Yu |
| 2014/0136814 A1 | 5/2014 | Stark |
| 2014/0140348 A1 | 5/2014 | Perlman |
| 2014/0143370 A1 | 5/2014 | Vilenski |
| 2014/0146819 A1 | 5/2014 | Bae |
| 2014/0149733 A1 | 5/2014 | Kim |
| 2014/0156396 A1 | 6/2014 | deKozan |
| 2014/0165207 A1 | 6/2014 | Engel |
| 2014/0172783 A1 | 6/2014 | Suzuki |
| 2014/0172981 A1 | 6/2014 | Kim |
| 2014/0173034 A1 | 6/2014 | Liu |
| 2014/0192717 A1 | 7/2014 | Liu |
| 2014/0195328 A1 | 7/2014 | Ferens |
| 2014/0195666 A1 | 7/2014 | Dumitriu |
| 2014/0233575 A1 | 8/2014 | Xie |
| 2014/0237085 A1 | 8/2014 | Park |
| 2014/0280823 A1 | 9/2014 | Varvello |
| 2014/0281489 A1 | 9/2014 | Peterka |
| 2014/0281505 A1 | 9/2014 | Zhang |
| 2014/0282816 A1 | 9/2014 | Xie |
| 2014/0289325 A1 | 9/2014 | Solis |
| 2014/0289790 A1 | 9/2014 | Wilson |
| 2014/0310298 A1* | 10/2014 | Stivoric ............. G06Q 30/0242 707/758 |
| 2014/0314093 A1 | 10/2014 | You |
| 2014/0365550 A1 | 12/2014 | Jang |
| 2015/0006896 A1 | 1/2015 | Franck |
| 2015/0018770 A1 | 1/2015 | Baran |
| 2015/0032892 A1 | 1/2015 | Narayanan |
| 2015/0063802 A1 | 3/2015 | Bahadur |
| 2015/0095481 A1 | 4/2015 | Ohnishi |
| 2015/0095514 A1 | 4/2015 | Yu |
| 2015/0188770 A1 | 7/2015 | Naiksatam |

FOREIGN PATENT DOCUMENTS

| | | | |
|---|---|---|---|
| EP | 0295727 A2 | 12/1988 | |
| EP | 0757065 A2 | 7/1996 | |
| EP | 1077422 A2 | 2/2001 | |
| EP | 1384729 A1 | 1/2004 | |
| EP | 2124415 A2 | 11/2009 | |
| EP | 2214357 A1 | 8/2010 | |
| WO | 03005288 A2 | 1/2003 | |
| WO | 03042254 A1 | 5/2003 | |
| WO | 03049369 A2 | 6/2003 | |
| WO | 03091297 A1 | 11/2003 | |
| WO | 2007113180 A1 | 10/2007 | |
| WO | 2007144388 A1 | 12/2007 | |
| WO | WO-2010108287 A1 * | 9/2010 | ........... A61B 5/1117 |
| WO | 2011049890 A1 | 4/2011 | |

OTHER PUBLICATIONS

Theodor Chris Panagiotakopoulos et al., "A Contextual Data Mining Approach Toward Assisting the Treatment of Anxiety Disorders", May 2010, IEEE Transactions on Information Technology in Biomedicine (vol. 14, Issue: 3, pp. 567-581) (Year: 2010).*

Xie et al. "Collaborative Forwarding and Caching in Content Centric Networks", Networking 2012.

Amadeo et al. "Design and Analysis of a Transport-Level Solution for Content-Centric VANETs", University "Mediterranea" of Reggio Calabria, Jun. 15, 2013.

Lui et al. (A TLV—Structured Data Naming Scheme for Content-Oriented Networking, pp. 5822-5827, International Workshop on the Network of the Future, Communications (ICC), 2012 IEEE International Conference on Jun. 10-15, 2012).

Jacobson, Van et al., "Content-Centric Networking, Whitepaper Describing Future Assurable Global Networks", Palo Alto Research Center, Inc., Jan. 30, 2007, pp. 1-9.

Koponen, Teemu et al., "A Data-Oriented (and Beyond) Network Architecture", SIGCOMM '07, Aug. 27-31, 2007, Kyoto, Japan, XP-002579021, p. 181-192.

Jacobson, Van et al. 'VoCCN: Voice Over Content-Centric Networks.' Dec. 1, 2009. ACM ReArch'09.

Rosenberg, J. "Interactive Connectivity Establishment (ICE): A Protocol for Network Address Translator (NAT) Traversal for Offer/Answer Protocols", Apr. 2010, pp. 1-117.

Shih, Eugene et al., 'Wake on Wireless: An Event Driven Energy Saving Strategy for Battery Operated Devices', Sep. 23, 2002, pp. 160-171.

Fall, K. et al., "DTN: an architectural retrospective", Selected areas in communications, IEEE Journal on, vol. 28, No. 5, Jun. 1, 2008, pp. 828-835.

Gritter, M. et al., 'An Architecture for content routing support in the Internet', Proceedings of 3rd Usenix Symposium on Internet Technologies and Systems, 2001, pp. 37-48.

"CCNx," http://ccnx.org/. downloaded Mar. 11, 2015.

"Content Delivery Network", Wikipedia, Dec. 10, 2011, http://en.wikipedia.org/w/index.php?title=Content_delivery_network&oldid=465077460.

"Digital Signature" archived on Aug. 31, 2009 at http://web.archive.org/web/20090831170721/http://en.wikipedia.org/wiki/Digital_signature.

"Introducing JSON," http://www.json.org/. downloaded Mar. 11, 2015.

"Microsoft PlayReady," http://www.microsoft.com/playready/. downloaded Mar. 11, 2015.

"Pursuing a pub/sub internet (PURSUIT)," http://www.fp7-pursuit.ew/PursuitWeb/. downloaded Mar. 11, 2015.

"The FP7 4WARD project," http://www.4ward-project.eu/. downloaded Mar. 11, 2015.

(56) References Cited

OTHER PUBLICATIONS

A. Broder and A. Karlin, "Multilevel Adaptive Hashing", Jan. 1990, pp. 43-53.
Detti, Andrea, et al. "CONET: a content centric inter-networking architecture." Proceedings of the ACM SIGCOMM workshop on Information-centric networking. ACM, 2011.
A. Wolman, M. Voelker, N. Sharma N. Cardwell, A. Karlin, and H.M. Levy, "On the scale and performance of cooperative web proxy caching," ACM SIGHOPS Operating Systems Review, vol. 33, No. 5, pp. 16-31, Dec. 1999.
Afanasyev, Alexander, et al. "Interest flooding attack and countermeasures in Named Data Networking." IFIP Networking Conference, 2013. IEEE, 2013.
Ao-Jan Su, David R. Choffnes, Aleksandar Kuzmanovic, and Fabian E. Bustamante. Drafting Behind Akamai: Inferring Network Conditions Based on CDN Redirections. IEEE/ACM Transactions on Networking (Feb. 2009).
B. Ahlgren et al., 'A Survey of Information-centric Networking' IEEE Commun. Magazine, Jul. 2012, pp. 26-36.
B. Lynn$2E.
Bari, MdFaizul, et al. 'A survey of naming and routing in information-centric networks.' Communications Magazine, IEEE 50.12 (2012): 44-53.
Baugher, Mark et al., "Self-Verifying Names for Read-Only Named Data", 2012 IEEE Conference on Computer Communications Workshops (INFOCOM WKSHPS), Mar. 2012, pp. 274-279.
Brambley, Michael, A novel, low-cost, reduced-sensor approach for providing smart remote monitoring and diagnostics for packaged air conditioners and heat pumps. Pacific Northwest National Laboratory, 2009.
C. Gentry and A. Silverberg. Hierarchical ID-Based Cryptography. Advances in Cryptology—ASIACRYPT 2002. Springer Berlin Heidelberg (2002).
C.A. Wood and E. Uzun, "Flexible end-to-end content security in CCN," in Proc. IEEE CCNC 2014, Las Vegas, CA, USA, Jan. 2014.
Carzaniga, Antonio, Matthew J. Rutherford, and Alexander L. Wolf. 'A routing scheme for content-based networking.' INFOCOM 2004. Twenty-third Annual Joint Conference of the IEEE Computer and Communications Societies. vol. 2. IEEE, 2004.
Cho, Jin-Hee, Ananthram Swami, and Ray Chen. "A survey on trust management for mobile ad hoc networks." Communications Surveys & Tutorials, IEEE 13.4 (2011): 562-583.
Compagno, Alberto, et al. "Poseidon: Mitigating interest flooding DDoS attacks in named data networking." Local Computer Networks (LCN), 2013 IEEE 38th Conference on. IEEE, 2013.
Conner, William, et al. "A trust management framework for service-oriented environments." Proceedings of the 18th international conference on World wide web. ACM, 2009.
Content Centric Networking Project (CCN) [online], http://ccnx.org/releases/latest/doc/technical/, Downloaded Mar. 9, 2015.
Content Mediator Architecture for Content-aware Networks (COMET) Project [online], http://www.comet-project.org/, Downloaded Mar. 9, 2015.
D. Boneh, C. Gentry, and B. Waters, 'Collusi.
D. Boneh and M. Franklin. Identity-Based Encryption from the Weil Pairing. Advances in Cryptology—CRYPTO 2001, vol. 2139, Springer Berlin Heidelberg (2001).
D.K. Smetters, P. Golle, and J.D. Thornton, "CCNx access control specifications," PARC, Tech. Rep., Jul. 2010.
Dabirmoghaddam, Ali, Maziar Mirzazad Barijough, and J. J. Garda-Luna-Aceves. 'Understanding optimal caching and opportunistic caching at the edge of information-centric networks,' Proceedings of the 1st international conference on Information-centric networking. ACM, 2014.
Detti et al., "Supporting the Web with an information centric network that routes by name", Aug. 2012, Computer Networks 56, pp. 3705-3702.
Dijkstra, Edsger W., and Carel S. Scholten. 'Termination detection for diffusing computations.' Information Processing Letters 11.1 (1980): 1-4.
Dijkstra, Edsger W., Wim HJ Feijen, and A_J M. Van Gasteren. "Derivation of a termination detection algorithm for distributed computations." Control Flow and Data Flow: concepts of distributed programming. Springer Berlin Heidelberg, 1986. 507-512.
E. Rescorla and N. Modadugu, "Datagram transport layer security," IETF RFC 4347, Apr. 2006.
E.W. Dijkstra, W. Feijen, and A.J.M. Van Gasteren, "Derivation of a Termination Detection Algorithm for Distributed Computations," Information Processing Letter, vol. 16, No. 5, 1983.
Fayazbakhsh, S. K, Lin, Y., Tootoonchian, A., Ghodsi, A., Koponen, T., Maggs, B., & Shenker, S. |Aug. 2013). Less pain, most of the gain: Incrementally deployable ICN. In ACM SIGCOMM Computer Communication Review (vol. 43, No. 4, pp. 147-158). ACM.
G. Ateniese, K. Fu, M. Green, and S. Hohenberger. Improved Proxy Reencryption Schemes with Applications to Secure Distributed Storage. In the 12th Annual Network and Distributed System Security Sympo.
G. Tyson, S. Kaune, S. Miles, Y. El-Khatib, A. Mauthe, and A. Taweel, "A trace-driven analysis of caching in content-centric networks," in Proc. IEEE ICCCN 2012, Munich, Germany, Jul.-Aug. 2012, pp. 1-7.
G. Wang, Q. Liu, and J. Wu, "Hierarchical attribute-based encryption for fine-grained access control in cloud storage services," in Proc. ACM CCS 2010, Chicago, IL, USA, Oct. 2010, pp. 735-737.
G. Xylomenos et al., "A Survey of Information-centric Networking Research," IEEE Communication Surveys and Tutorials, Jul. 2013.
Garcia, Humberto E., Wen-Chiao Lin, and Semyon M. Meerkov. "A resilient condition assessment monitoring system." Resilient Control Systems (ISRCS), 2012 5th International Symposium on. IEEE, 2012.
Garcia-Luna-Aceves, Jose J. 'A unified approach to loop-free routing using distance vectors or link states.' ACM SIGCOMM Computer Communication Review. vol. 19. No. 4. ACM, 1989.
Garcia-Luna-Aceves, Jose J. 'Name-Based Content Routing in Information Centric Networks Using Distance Information' Proc ACM ICN 2014, Sep. 2014.
Ghali, Cesar, GeneTsudik, and Ersin Uzun. "Needle in a Haystack: Mitigating Content Poisoning in Named-Data Networking." Proceedings of NDSS Workshop on Security of Emerging Networking Technologies (SENT). 2014.
Ghodsi, Ali, et al. "Information-centric networking: seeing the forest for the trees." Proceedings of the 10th ACM Workshop on Hot Topics in Networks. ACM, 2011.
Ghodsi, Ali, et al. "Naming in content-oriented architectures." Proceedings of the ACM SIGCOMM workshop on Information-centric networking. ACM, 2011.
Gupta, Anjali, Barbara Liskov, and Rodrigo Rodrigues. "Efficient Routing for Peer-to-Peer Overlays." NSDI. vol. 4. 2004.
H. Xiong, X. Zhang, W. Zhu, and D. Yao. CloudSeal: End-to$2.
Heckerman, David, John S. Breese, and Koos Rommelse. "Decision-Theoretic Troubleshooting." Communications of the ACM. 1995.
Heinemeier, Kristin, et al. "Uncertainties in Achieving Energy Savings from HVAC Maintenance Measures in the Field." ASHRAE Transactions 118.Part 2 {2012).
Herlich, Matthias et al., "Optimizing Energy Efficiency for Bulk Transfer Networks", Apr. 13, 2010, pp. 1-3, retrieved for the Internet. URL:http://www.cs.uni-paderborn.de/fileadmin/informationik/ag-karl/publications/miscellaneous/optimizing.pdf (retrieved on Mar. 9, 2012).
Hoque et al., 'NLSR: Named-data Link State Routing Protocol', Aug. 12, 2013, ICN 2013, pp. 15-20.
https://code.google.com/p/ccnx-trace/.
I. Psaras, R.G. Clegg, R. Landa, W.K. Chat, and G. Pavlou, "Modelling and evaluation of CCN-caching trees," in Proc. IFIP Networking 2011, Valencia, Spain, May 2011, pp. 78-91.
Intanagonwiwat, Chalermek, Ramesh Govindan, and Deborah Estrin. 'Directed diffusion: a scalable and robust communication paradigm for sensor networks.' Proceedings of the 6th annual international conference on Mobile computing and networking. ACM, 2000.
J. Aumasson and D. Bernstein, "SipHash: a fast short-input PRF", Sep. 18, 2012.

(56) References Cited

OTHER PUBLICATIONS

J. Bethencourt, A, Sahai, and B. Waters, 'Ciphertext-policy attribute-based encryption,' in Proc. IEEE Security & Privacy 2007, Berkeley, CA, USA, May 2007, pp. 321-334.
J. Hur, "Improving security and efficiency in attribute-based data sharing," IEEE Trans. Knowledge Data Eng., vol. 25, No. 10, pp. 2271-2282, Oct. 2013.
J. Shao and Z. Cao. CCA-Secure Proxy Re-Encryption without Pairings. Public Key Cryptography. Springer Lecture Notes in Computer Sciencevol. 5443 (2009).
V. Jacobson et al., 'Networking Named Content,' Proc. IEEE CoNEXT '09, Dec. 2009.
Jacobson et al., "Custodian-Based Information Sharing," Jul. 2012, IEEE Communications Magazine: vol. 50 Issue 7 (p. 3843).
Ji, Kun, et al. "Prognostics enabled resilient control for model-based building automation systems." Proceedings of the 12th Conference of International Building Performance Simulation Association. 2011.
K. Liang, L. Fang, W. Susilo, and D.S. Wong, "A Ciphertext-policy attribute-based proxy re-encryption with chosen-ciphertext security," in Proc. INCoS 2013, Xian, China, Sep. 2013, pp. 552-559.
Katipamula, Srinivas, and Michael R. Brambley. "Review article: methods for fault detection, diagnostics, and prognostics for building systemsa review, Part I." HVAC&R Research 11.1 (2005): 3-25.
Katipamula, Srinivas, and Michael R. Brambley. "Review article: methods for fault detection, diagnostics, and prognostics for building systemsa review, Part II." HVAC&R Research 11.2 (2005): 169-187.
L. Wang et al., 'OSPFN: An OSPF Based Routing Protocol for Named Data Networking,' Technical Report NDN-0003, 2012.
L. Zhou, V. Varadharajan, and M. Hitchens, "Achieving secure role-based access control on encrypted data in cloud storage," IEEE Trans. Inf. Forensics Security, vol. 8, No. 12, pp. 1947-1960, Dec. 2013.
Li, Wenjia, Anupam Joshi, and Tim Finin. "Coping with node misbehaviors in ad hoc networks: A multi-dimensional trust management approach." Mobile Data Management (MDM), 2010 Eleventh International Conference on. IEEE, 2010.
Lopez, Javier, et al. "Trust management systems for wireless sensor networks: Best practices." Computer Communications 33.9 (2010): 1086-1093.
M. Blaze, G. Bleumer, and M. Strauss, 'Divertible protocols and atomic prosy cryptography,' in Proc. EUROCRYPT 1998, Espoo, Finland, May-Jun. 1998, pp. 127-144.
M. Green and G. Ateniese, "Identity-based proxy re-encryption," in Proc. ACNS 2007, Zhuhai, China, Jun. 2007, pp. 288-306.
M. Ion, J. Zhang, and E.M. Schooler, "Toward content-centric privacy in ICN: Attribute-based encryption and routing," in Proc. ACM SIGCOMM ICN 2013, Hong Kong, China, Aug. 2013, pp. 39-40.
M. Naor and B. Pinkas "Efficient trace and revoke schemes," in Proc. FC 2000, Anguilla, British West Indies, Feb. 2000, pp. 1-20.
M. Nystrom, S. Parkinson, A. Rusch, and M. Scott, "PKCS#12: Personal information exchange syntax v. 1.1," IETF RFC 7292, K. Moriarty, Ed., Jul. 2014.
M. Parsa and J.J. Garcia-Luna-Aceves, "A Protocol for Scalable Loop-free Multicast Routing." IEEE JSAC, Apr. 1997.
M. Walfish, H. Balakrishnan, and S. Shenker, "Untangling the web from DNS," in Proc. USENIX NSDI 2004, Oct. 2010, pp. 735-737.
Mahadevan, Priya, et al. "Orbis: rescaling degree correlations to generate annotated internet topologies." ACM SIGCOMM Computer Communication Review. vol. 37. No. 4. ACM, 2007.
Mahadevan, Priya, et al. "Systematic topology analysis and generation using degree correlations." ACM SIGCOMM Computer Communication Review. vol. 36. No. 4. ACM, 2006.
Matocha, Jeff, and Tracy Camp. 'A taxonomy of distributed termination detection algorithms.' Journal of Systems and Software 43.3 (1998): 207-221.
Matteo Varvello et al., "Caesar: A Content Router for High Speed Forwarding", ICN 2012, Second Edition on Information-Centric Networking, New York, Aug. 2012.
McWilliams, Jennifer A., and Iain S. Walker. "Home Energy Article: A Systems Approach to Retrofitting Residential HVAC Systems." Lawrence Berkeley National Laboratory (2005).
Merindol et al., "An efficient algorithm to enable path diversity in link state routing networks", Jan. 10, Computer Networks 55 (2011), pp. 1132-1140.
Mobility First Project [online], http://mobilityfirst.winlab.rutgers.edu/, Downloaded Mar. 9, 2015.
Narasimhan, Sriram, and Lee Brownston. "HyDE—A General Framework for Stochastic and Hybrid Modelbased Diagnosis." Proc. DX 7 (2007): 162-169.
NDN Project [online], http://www.named-data.net/, Downloaded Mar. 9, 2015.
Omar, Mawloud, Yacine Challal, and Abdelmadjid Bouabdallah. "Certification-based trust models in mobile ad hoc networks: A survey and taxonomy." Journal of Network and Computer Applications 35.1 (2012): 268-286.
P. Mahadevan, E.Uzun, S. Sevilla, and J. Garcia-Luna-Aceves, "CCN-krs: A key resolution service for ccn," in Proceedings of the 1st International Conference on Information-centric Networking, Ser. INC 14 New York, NY, USA: ACM, 2014, pp. 97-106. [Online]. Available: http://doi.acm.org/10.1145/2660129.2660154.
R. H. Deng, J. Weng, S. Liu, and K. Chen. Chosen-Ciphertext Secure Proxy Re-Encryption without Pairings. CANS. Spring Lecture Notes in Computer Science vol. 5339 (2008).
S. Chow, J. Weng, Y. Yang, and R. Deng. Efficient Unidirectional Proxy Re-Encryption. Progress in Cryptology—AFRICACRYPT 2010. Springer Berlin Heidelberg (2010).
S. Deering, "Multicast Routing in Internetworks and Extended LANs," Proc. ACM SIGCOMM '88, Aug. 1988.
S. Deering et al., "The PIM architecture for wide-area multicast routing," IEEE/ACM Trans, on Networking, vol. 4, No. 2, Apr. 1996.
S. Jahid, P. Mittal, and N. Borisov, "EASiER: Encryption-based access control in social network with efficient revocation," in Proc. ACM ASIACCS 2011, Hong Kong, China, Mar. 2011, pp. 411-415.
S. Kamara and K. Lauter, "Cryptographic cloud storage," in Proc. FC 2010, Tenerife, Canary Islands, Spain, Jan. 2010, pp. 136-149.
S. Kumar et al. "Peacock Hashing: Deterministic and Updatable Hashing for High Performance Networking," 2008, pp. 556-564.
S. Misra, R. Tourani, and N.E. Majd, "Secure content delivery in information-centric networks: Design, implementation, and analyses," in Proc. ACM SIGCOMM ICN 2013, Hong Kong, China, Aug. 2013, pp. 73-78.
S. Yu, C. Wang, K. Ren, and W. Lou, "Achieving secure, scalable, and fine-grained data access control in cloud computing," in Proc. IEEE INFOCOM 2010, San Diego, CA, USA, Mar. 2010, pp. 1-9.
S.J. Lee, M. Gerla, and C. Chiang, "On-demand Multicast Routing Protocol in Multihop Wireless Mobile Networks," Mobile Networks and Applications, vol. 7, No. 6, 2002.
Sandvine, Global Internet Phenomena Report—Spring 2012. Located online at http://www.sandvine.com/downloads/ documents/ Phenomenal H 2012/Sandvine Global Internet Phenomena Report 1H 2012.pdf.
Scalable and Adaptive Internet Solutions (SAIL) Project [online], http://sail-project.eu/ Downloaded Mar. 9, 2015.
Schein, Jeffrey, and Steven T. Bushby. A Simulation Study of a Hierarchical, Rule-Based Method for System-Level Fault Detection and Diagnostics in Hvac Systems. US Department of Commerce,[Technology Administration], National Institute of Standards and Technology, 2055.
Shani, Guy, Joelle Pineau, and Robert Kaplow. "A survey of point-based POMDP solvers." Autonomous Agents and Multi-Agent Systems 27.1 (2013): 1-51.
Sheppard, John W., and Stephyn GW Butcher. "A formal analysis of fault diagnosis with d-matrices." Journal of Electronic Testing 23.4 (2007): 309-322.
Shneyderman, Alex et al., 'Mobile VPN: Delivering Advanced Services in Next Generation Wireless Systems', Jan. 1, 2003, pp. 3-29.
Solis, Ignacio, and J. J. Garcia-Luna-Aceves. 'Robust content dissemination in disrupted environments.' proceedings of the third ACM workshop on Challenged networks. ACM, 2008.

(56) References Cited

OTHER PUBLICATIONS

Sun, Ying, and Daniel S. Weld. "A framework for model-based repair." AAAI. 1993.

T. Ballardie, P. Francis, and J. Crowcroft, "Core Based Trees (CBT)," Proc. ACM SIGCOMM '88, Aug. 1988.

T. Dierts, "The transport layer security (TLS) protocol version 1.2," IETF RFC 5246, 2008.

T. Koponen, M. Chawla, B.-G. Chun, A. Ermolinskiy, K.H. Kim, S. Shenker, and I. Stoica, 'A data-oriented (and beyond) network architecture,' ACM SIGCOMM Computer Communication Review, vol. 37, No. 4, pp. 181-192, Oct. 2007.

The Despotify Project (2012). Available online at http://despotify.sourceforge.net/.

V. Goyal, 0. Pandey, A. Sahai, and B. Waters, "Attribute-based encryption for fine-grained access control of encrypted data," in Proc. ACM CCS 2006, Alexandria, VA, USA, Oct.-Nov. 2006, pp. 89-98.

V. Jacobson, D.K. Smetters, J.D. Thornton, M.F. Plass, N.H. Briggs, and R.L. Braynard, 'Networking named content,' in Proc. ACM CoNEXT 2009, Rome, Italy, Dec. 2009, pp. 1-12.

V. K. Adhikari, S. Jain, Y. Chen, and Z.-L. Zhang. Vivisecting Youtube:An Active Measurement Study. In INFOCOM12 Miniconference (2012).

Verma, Vandi, Joquin Fernandez, and Reid Simmons. "Probabilistic models for monitoring and fault diagnosis." The Second IARP and IEEE/RAS Joint Workshop on Technical Challenges for Dependable Robots in Human Environments. Ed. Raja Chatila. Oct. 2002.

Vijay Kumar Adhikari, Yang Guo, Fang Hao, Matteo Varvello, Volker Hilt, Moritz Steiner, and Zhi-Li Zhang. Unreeling Netflix: Understanding and Improving Multi-CDN Movie Delivery. In the Proceedings of IEEE INFOCOM 2012 (2012).

Vutukury, Srinivas, and J. J. Garcia-Luna-Aceves. A simple approximation to minimum-delay routing. vol. 29. No. 4. ACM, 1999.

W.-G. Tzeng and Z.-J. Tzeng, "A public-key traitor tracing scheme with revocation using dynamic shares," in Proc. PKC 2001, Cheju Island, Korea, Feb. 2001, pp. 207-224.

Waldvogel, Marcel "Fast Longest Prefix Matching: Algorithms, Analysis, and Applications", A dissertation submitted to the Swiss Federal Institute of Technology Zurich, 2002.

Walker, Iain S. Best practices guide for residential HVAC Retrofits. No. LBNL-53592. Ernest Orlando Lawrence Berkeley National Laboratory, Berkeley, CA (US), 2003.

Wang, Jiangzhe et al., "DMND: Collecting Data from Mobiles Using Named Data", Vehicular Networking Conference, 2010 IEEE, pp. 49-56.

Xylomenos, George, et al. "A survey of information-centric networking research." Communications Surveys & Tutorials, IEEE 16.2 (2014): 1024-1049.

Yi, Cheng, et al. 'A case for stateful forwarding plane.' Computer Communications 36.7 (2013): 779-791.

Yi, Cheng, et al. 'Adaptive forwarding in named data networking.' ACM SIGCOMM computer communication review 42.3 (2012): 62-67.

Zahariadis, Theodore, et al. "Trust management in wireless sensor networks." European Transactions on Telecommunications 21.4 (2010): 386-395.

Zhang, et al., "Named Data Networking (NDN) Project", http://www.parc.com/publication/2709/named-data-networking-ndn-project.html, Oct. 2010, NDN-0001, PARC Tech Report.

Zhang, Lixia, et al. 'Named data networking.' ACM SIGCOMM Computer Communication Review 44.3 {2014): 66-73.

Soh et al., "Efficient Prefix Updates for IP Router Using Lexicographic Ordering and Updateable Address Set", Jan. 2008, IEEE Transactions on Computers, vol. 57, No. 1.

Beben et al., "Content Aware Network based on Virtual Infrastructure", 2012 13th ACIS International Conference on Software Engineering.

Biradar et al., "Review of multicast routing mechanisms in mobile ad hoc networks", Aug. 16, Journal of Network$.

D. Trossen and G. Parisis, "Designing and realizing and information-centric internet", IEEE Communications Magazing, vol. 50, No. 7, pp. 60-67, Jul. 2012.

Garcia-Luna-Aceves et al., "Automatic Routing Using Multiple Prefix Labels", 2012, IEEE, Ad Hoc and Sensor Networking Symposium.

Gasti, Paolo et al., 'DoS & DDoS in Named Data Networking', 2013 22nd International Conference on Computer Communications and Networks (ICCCN), Aug. 2013, pp. 1-7.

Ishiyama, "On the Effectiveness of Diffusive Content Caching in Content-Centric Networking", Nov. 5, 2012, IEEE, Information and Telecommunication Technologies (APSITT), 2012 9th Asia-Pacific Symposium.

J. Hur and D.K. Noh, "Attribute-based access control with efficient revocation in data outsourcing systers," IEEE Trans. Parallel Distrib. Syst, vol. 22, No. 7, pp. 1214-1221, Jul. 2011.

J. Lotspiech, S. Nusser, and F. Pestoni. Anonymous Trust: Digital Rights Management using Broadcast Encryption. Proceedings of the IEEE 92.6 (2004).

Kaya et al., "A Low Power Lookup Technique for Multi-Hashing Network Applications", 2006 IEEE Computer Society Annual Symposium on Emerging VLSI Technologies and Architectures, Mar. 2006.

S. Kamara and K. Lauter. Cryptographic Cloud Storage. Financial Cryptography and Data Security. Springer Berlin Heidelberg (2010).

RTMP (2009). Available online at http://wwwimages.adobe.com/www.adobe.com/content/dam/Adobe/en/devnet/rtmp/ pdf/rtmp specification 1.0.pdf.

Hoque et al., "NLSR: Named-data Link State Routing Protocol", Aug. 12, 2013, ICN'13.

Nadeem Javaid, "Analysis and design of quality link metrics for routing protocols in Wireless Networks", PhD Thesis Defense, Dec. 15, 2010, Universete Paris-Est.

Wetherall, David, "Active Network vision and reality: Lessons form a capsule-based system", ACM Symposium on Operating Systems Principles, Dec. 1, 1999. pp. 64-79.

Kulkarni A.B. et al., "Implementation of a prototype active network", IEEE, Open Architectures and Network Programming, Apr. 3, 1998, pp. 130-142.

\* cited by examiner

300

1. ANXIETY
2. WORRY
3. SHORTNESS OF BREATH
4. RACING/POUNDING HEART
5. DIZZINESS/FAINTNESS
6. CHEST PAIN/DISCOMFORT
7. FEELINGS OF UNREALITY
8. SWEATING
9. HOT FLASHES/COLD FLASHES
10. FEAR OF LOSING CONTROL/SANITY
11. TREMBLING/SHAKING
12. CHOKING SENSATIONS
13. NAUSEA
14. NUMBNESS/TINGLING
15. FEAR OF DYING

302

SYMPTOM SEVERITY SCALE
1. NONE
2. MILD
3. MODERATE
4. STRONG
5. EXTREME

|  | | User 1 | User 2 | User 3 | User 4 | User 5 | User 6 | User 7 | Total |
|---|---|---|---|---|---|---|---|---|---|
| NON-PANIC EPISODES | ¬PA | 65 | 20 | 5 | 42 | 28 | 69 | 51 | 280 |
| PANIC EPISODES | PA | 1 | 4 | 2 | 10 | 0 | 0 | 0 | 17 |
| TOTAL | | 66 | 24 | 7 | 52 | 28 | 69 | 51 | 297 |

FIG. 10

| Precision | 0.938 |
| Recall | 0.838 |
| $F_1$ Score | 0.885 |

|              | ACTUAL OUTCOME ||
|PREDICTION| PA | ¬PA |
|---|---|---|
| PA | 0 | 2 |
| ¬PA | 0 | 10 |

1602

|              | ACTUAL OUTCOME ||
|PREDICTION| PA | ¬PA |
|---|---|---|
| PA | 0 | 0 |
| ¬PA | 0 | 28 |

1604

|              | ACTUAL OUTCOME ||
|PREDICTION| PA | ¬PA |
|---|---|---|
| PA | 0 | 0 |
| ¬PA | 0 | 22 |

INTERACTIVE REMOTE PATIENT MONITORING AND CONDITION MANAGEMENT INTERVENTION SYSTEM

FIELD

The present disclosure generally relates to interactive remote health monitoring. More specifically, the present disclosure relates to a method and system for monitoring a user's physiological condition to deliver healthcare management recommendations in real-time.

RELATED ART

Individuals may have health issues that require monitoring and care. Different individuals may have personal health concerns that require appropriate levels of monitoring. Depending on the particular health problem, one individual may require in-hospital care, while another only needs to self-monitor his or her condition.

A user may use a remote patient monitoring system to monitor the user's physiological condition and send medical data to a clinical care team that is monitoring the user remotely. Other users may be able to monitor their physiological condition on their own but unfortunately current systems may only present healthcare data, and do not provide adequate support to the user. Furthermore, some systems require users to wear multiple types of intrusive physiological monitoring equipment which is not suitable for everyday life.

SUMMARY

One embodiment of the present invention provides a method for generating a personalized health management recommendation for a user. During operation, the system obtains first physiological data, generated by a wearable device worn by the user, that indicates a physiological condition of the user. The system then generates a prediction model for the user based on the first physiological data. The system obtains real-time physiological data generated by the wearable device. The system may generate a prediction by analyzing the real-time physiological data to determine whether the user's physiological condition exceeds a threshold parameter according to the prediction model. Upon determining that the threshold parameter has been exceeded, the system selects a recommendation, and sends the recommendation message to the user's mobile device.

In one variation on this embodiment, generating the prediction model further includes generating at least one regression model for the user using second physiological data obtained while the user is performing physical activities without any panic attacks.

In a further variation, generating the prediction model further comprises generating panic matrices and non-panic matrices from the first physiological data, and generating one or more delta matrices using the at least one regression model and the panic matrices and non-panic matrices. A delta matrix represents a difference between expected values of physiological data with an amount of physical activity and actual physiological values observed.

In one variation on this embodiment, the system determines a change point within a respective time-series data of each physiological variable to generate change point matrices.

In a further variation, the system generates, based on at least one change point matrix, summary statistics that include at least a mean, a standard deviation, and a number of change points for each physiological measurement type obtained from the wearable device.

In one variation on this embodiment, the prediction model predicts that the user is likely to suffer a panic attack within an hour.

In a further variation on this embodiment, the system obtains real-time contextual data that indicates a current context for the user, and wherein generating the prediction further comprises accounting for the contextual data to improve the accuracy of predictions.

BRIEF DESCRIPTION OF THE FIGURES

FIG. 10 presents a table illustrating the total number of non-panic and panic instances included in the analysis for each user.

FIG. 16 illustrates the confusion matrix results for Users 5, 6 and 7.

In the figures, like reference numerals refer to the same figure elements.

DETAILED DESCRIPTION

Figure 1:
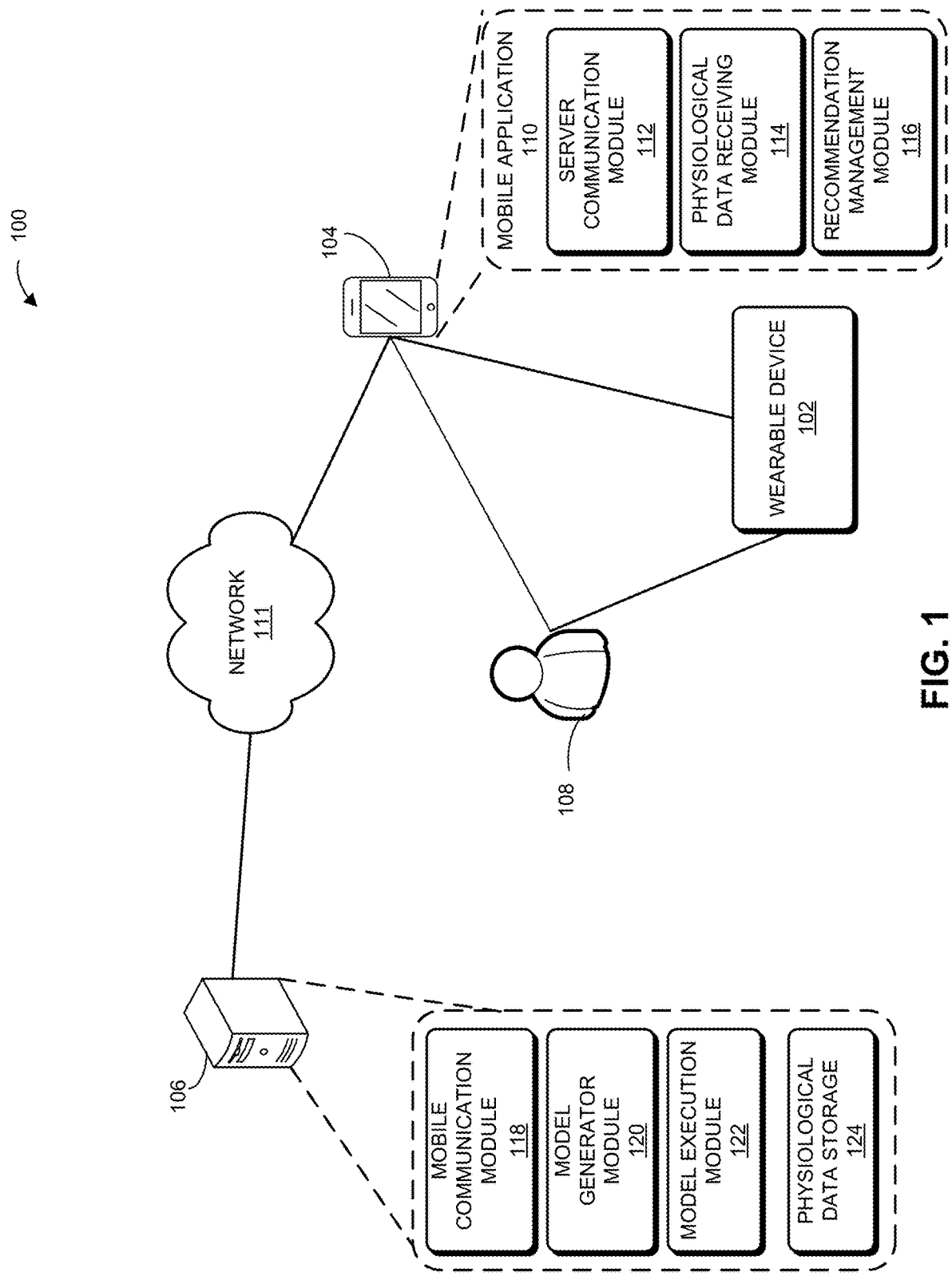
FIG. 1 presents a diagram illustrating an exemplary interactive remote health monitoring system, in accordance with an embodiment of the present invention.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

Overview

Embodiments of the present invention solve the problem of assisting users with managing health issues by remotely monitoring a user's physiological condition and context to predict upcoming health conditions and provide personalized care management recommendations in real-time. For example, a user may suffer from panic episodes and receive support recommendations for managing a predicted impending panic episode. An interactive remote health monitoring system can gather data from multiple sources to facilitate accurate analysis of user physiological data and generate actionable recommendations to send to the user's mobile device. The health monitoring system may detect approaching panic episodes before such panic episodes occur, in order to deliver in-the-moment mobile-based recommendations.

The interactive remote health monitoring system combines a personal wearable device with a mobile device (e.g., smartphone) application to interactively help the user react to and cope with panic attacks. The wearable device may continuously collect real-time physiological data about a user and communicate with the mobile application. The system may obtain data from the wearable device and generate a personalized prediction model for each user to account for physiological differences between individuals. The system may also obtain context data from multiple other sources in order to account for contextual factors, such as the user's environment, to improve the accuracy of predictions. In some instances, the system may determine that certain physiological changes are not caused by a panic attack but rather are due to a user's activity or context (e.g. the surrounding environment).

One implementation of the system is aimed at people who suffer from panic disorder and experience regular and spontaneous panic attacks. The system automatically detects impending panic attacks by monitoring changes in the user's vital signs. Changes in the user's physiology may begin to take place up to one hour before the onset of a panic attack and users are usually not aware that these changes are taking place until they experience (what to them feels like) the "spontaneous" symptoms of a panic attack. By continuously monitoring physiological data such as heart rate, breathing rate, heart rate variability and temperature, the system is able to distinguish between the pre-panic and non-panic intervals.

The system can help users manage their health while they are not under direct medical supervision. This can help the user respond to and cope with panic episode symptoms. Such a system can help to manage a user's condition by reducing the severity or intensity of symptoms and reduce the possibility of complications, and also improve the user's mental health and well-being.

In some implementations, the system can assist users with managing other conditions such as post-traumatic stress syndrome (PTSD), heart disease, and other chronic conditions. Some implementations can also assist with detecting stress, fatigue, or sleepiness for individuals in various jobs. Examples of such jobs may include drivers, pilots, surgeons, software developers, air traffic controllers, firefighters and machine operators. These systems can send recommendations to help keep the user alert and achieve the goals of productivity and safety. Furthermore, some systems can provide recommendations to world-class athletes to assist with controlling their eating, sleeping, or drinking to achieve their goals in sports.

The Study

The inventors performed a data collection study where they asked individuals who suffered from panic disorder to use a wearable device that continuously monitored their vital signs in day-to-day life for up to three weeks. The study participants used a mobile application to report when they experienced a panic attack. The study participants also reported information about the severity of the symptoms they experienced during attacks.

Below is a description of an exemplary implementation of an interactive remote health monitoring system and physiological dataset generated from the study. The system trains prediction models which take, as input, physiological data and outputs a binary classification of either pre-panic or non-panic. The description explains how the system may use the physiological data to train the panic prediction models, and provides specific examples of how the system processed data from the study and the results of performing statistical analysis on the collected dataset.

The description below describes determining change points and provides examples of determining change points for data from the study. The system may locate the position and magnitude of significant change points in the physiological data and use this information in a supervised anomaly detection technique to predict approaching panic episodes. A change point is an instance in time where the statistical properties of a sequence of observations change. The system may apply change-point detection to locate points in a time-series where significant changes occur. A series of physiological changes occur up to one hour before an individual experiences any symptoms related to a panic episode. During this period the individual is not aware of any symptoms until the moment she experiences an "out-of-the-blue" panic attack. Vital sign measurements such as heart rate, $pCO_2$ (the amount of carbon dioxide in the blood), tidal volume (the volume of air moved into or out of the lungs), respiration rate and heart rate variability all exhibit one or more change points in the hour preceding a reported panic episode. In contrast, regular measurements without any panic episodes exhibit none or relatively few change points.

The description below also provides examples of accounting for physical activity in the study. This disclosure describes how the system may account for variables such as physical activity and user context, which affect physiological measurements and therefore prediction accuracy. By accounting for physical activity and context, the system can reduce false positives.

The description below also evaluates the model and presents the precision/recall results the system achieved on held-out test data from the study. The precision for a class is the number of true positives divided by the total number of elements labeled as belonging to the positive class (e.g. the sum of true positives and false positives). Recall is the number of true positives divided by the total number of elements that actually belong to the positive class. On average, for predicting upcoming panic episodes, the system was able to achieve precision of 93.8% and recall of 83.8%, giving an overall $F_1$ score of 88.5%. Note that the $F_1$ score is a measure of accuracy and can be interpreted as a weighted average of the precision and recall.

Exemplary Interactive Remote Health Monitoring System

FIG. 1 presents a diagram illustrating an exemplary interactive remote health monitoring system 100, in accordance with an embodiment of the present invention. Interactive remote health monitoring system 100 is a mobile and wearable system that the user can take anywhere while performing his regular routines. System 100 combines a personal wearable device with a mobile device application that allows a user to cope with health problems, such as panic attacks. The wearable device collects real-time physiological data about the user and communicates with a mobile application. The system automatically detects impending panic attacks by monitoring changes in the user's vital signs. The system may monitor physiological changes occurring up to one hour before the user is aware that he is experiencing panic attack symptoms.

System 100 includes a number of computing devices, such as a wearable device 102, a mobile device 104, and a server 106. Wearable device 102 can be any type of a device equipped with sensors that monitor, detect, and/or record the user's physiological condition. Wearable device is typically worn on the chest or on the wrist, but can be worn anywhere on the body. For example, wearable device 102 can be a Zephyr BioPatch™ wireless sensor device. In some implementations, wearable device 102 can also generate some of the user's contextual data, including Global Positioning System (GPS) location coordinate data and time and date. System 100 can obtain the user's contextual data, including environmental data, from other sensors and/or other different sources that provide the data. For example, system 100 may obtain data describing environmental conditions surrounding the user, such as air pressure, oxygen level in the air, and air quality (e.g., pollution level, smog level). System 100 may obtain such data from building sensors or other available environmental sensors.

Wearable device 102 can attach to a user 108 and continuously collect real-time physiological data about user 108. During a panic attack, a user may experience shortness of breath, increased heart rate, dizziness, chest pain, sweating, hot flashes, trembling, choking, nausea, and numbness. The user may also have feelings of unreality, a fear of losing control and a fear of dying. The majority of these symptoms are physiological in nature, and hence are detectable through physiological measurements such as heart rate, respiration rate, perspiration and skin temperature. These physiological measurements are detectable using wearable device 102.

Wearable device 102 communicates with a mobile application 110 executing on mobile device 104 to provide physiological data about user 108 in real-time. Wearable device 102 may provide data describing the user's physiological condition, including heart rate, respiration rate, heart rate variability, core temperature, and activity. Some wearable devices may also provide data such as galvanic skin response, tidal volume, and $pCO_2$. In one implementation, wearable device 102 can sample the user's physiological measurements at a rate of approximately 1 Hz. Other sampling rates are also possible in different implementations.

Mobile device 104 can be any type of a mobile computing device, such as a smartphone, a personal digital assistant (PDA), or a tablet. Mobile device 104 also includes a mobile application 110 which communicates via Bluetooth with wearable device 102. Mobile application 110 sends physiological data to server 106 through network 111, and server 106 processes the data. In some implementations, mobile application 110 may include a sever communication module 112, a physiological data receiving module 114, and a recommendation management module 116.

Server communication module 112 may send physiological data to server 106. Physiological data receiving module 114 receives the physiological data from wearable device 102. Recommendation management module 116 receives recommendations from server 106 and displays the recommendations to user 108 on mobile device 104. Recommendation management module 116 may display a message and/or read the message to user 108. Recommendation management module 116 may also receive user feedback regarding the recommendations and user symptoms, and server communication module 112 may send the feedback to server 106. Server 106 may improve the prediction model using the feedback from user 108. User 108 may also report panic episodes and server 106 may improve the prediction model based on reports from user 108.

In some implementations, server 106 may send recommendations to a separate mobile device that may be operated by a second user such as a medical provider, nurse, parent, or coach. The second user may use the separate mobile device to monitor and assist user 108 and also receive recommendations from server 106 on how to assist or coach user 108.

In some implementations, user 108 can choose to receive a mobile-based recommendation that she feels most comfortable with. One example of such a recommendation is respiratory biofeedback. In respiratory biofeedback, system 100 delivers breathing and relaxation exercise instructions to a user who can visually monitor the effect breathing exercises have on the user's vital signs using the user's mobile device. Some studies have shown respiratory biofeedback to be effective at alleviating short term panic attack symptoms and may also make people less prone to future panic attacks. The user may receive a recommendation to follow breathing and relaxation exercises using a biofeedback mobile application.

Other examples of recommendations user 108 may select from include musical therapy, exercise therapy, and social therapy. For musical therapy, a user can preselect a personalized musical playlist to listen to on their phone in the event of an approaching episode. For exercise therapy, system 100 can prompt a user to perform a preselected exercise routine. In some implementations, the system may detect the user is sleepy and sends a recommendation to exercise to the user (e.g., a software developer or a pilot). The user can take a break and exercise, thereby reducing the likelihood of introducing new bugs in software or having an accident while flying. For social therapy, system 100 can give the user a suggestion to change their environment or seek out family, friends or colleagues to talk to.

Server 106 analyzes the physiological information and provides real-time recommendations to user 108 by sending recommendations to mobile device 104. In some implementations, server 106 may include a mobile communication module 118, a model generator module 120, a model execution module 122, and a physiological data storage 124. Mobile communication module 118 sends recommendations to mobile device 104 and receives physiological data from mobile device 104. Model generator module 120 generates a prediction model for user 108 based on physiological data associated with user 108 and activity data. Model execution module 122 uses the generated model to analyze the user's physiological data and contextual data to predict panic attacks. Physiological data storage 124 stores physiological data for user 108.

Server 106 may analyze the physiological data to detect whether the user will experience an upcoming panic attack. When analyzing the physiological data, server 100 may account for the effect physical activity and user context has on the physiological measurements. In the event that server 106 determines that the user will experience a panic attack, server 106 sends recommendations, which are personalized messages generated for user 108, to mobile application 110. The recommendations are typically actionable messages that notify the user of an impending change in the user's physiological condition, such as a panic attack. Note that server 106 may provide services to a plurality of users that include user 108. In some implementations, the operations performed by server 106 are performed by one or more modules operating in mobile device 104.

Generating a Prediction Model

Figure 2:
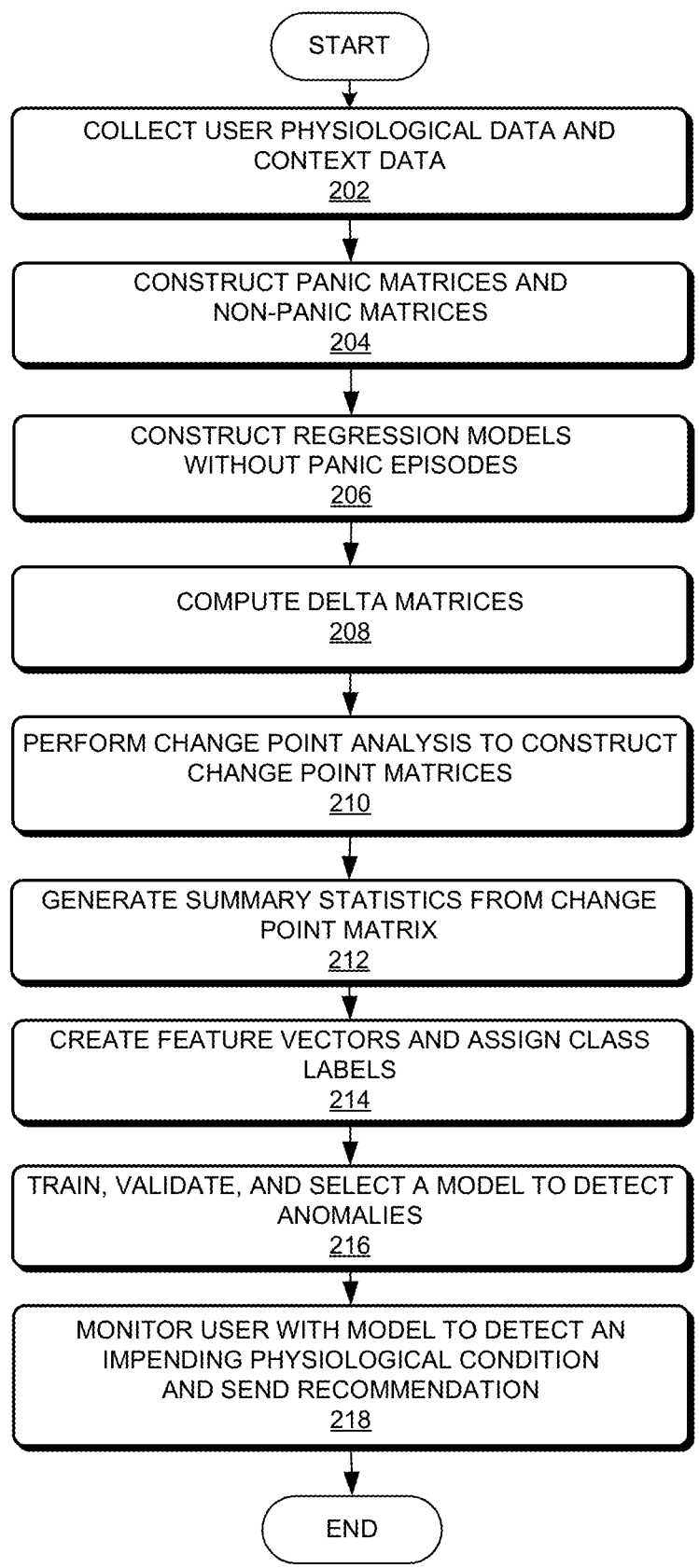
FIG. 2 presents a flow chart illustrating an exemplary process to generate a model for interactive remote health monitoring, in accordance with an embodiment of the present invention.

FIG. 2 presents a flow chart illustrating an exemplary process to generate a model for interactive remote health monitoring, in accordance with an embodiment of the present invention. The depicted process is for monitoring users that suffer from panic episodes, and one can adapt the process to monitor users for other physiological conditions.

As depicted in FIG. 2, the system may initially collect user physiological data and contextual data, including environmental data (operation 202). The system may receive the physiological data from the user's wearable device. The system may receive the contextual data from multiple sensors and/or other sources. For example, the system may receive data indicating air pressure, weather, air pollution level, or other such environmental data from different sensors. In some implementations, the wearable device may also provide some of the contextual data, such as GPS or air pressure.

The system then constructs panic matrices and non-panic matrices (operation 204). The system may extract a time-slice surrounding each reported panic episode and non-panic episode. The system may perform a rollup by computing average values for each one minute interval and interpolate missing values.

Next, the system constructs regression models without panic episodes (operation 206). The system constructs the regression models for the user from data collected when the user did not experience any panic episodes and performed some physical activity. The system then computes delta matrices (operation 208). The system uses the delta matrices to account for physical activity in the model.

The system may perform change point analysis to construct change point matrices (operation 210). The system may then generate summary statistics from the change point matrix $CP(D^k)$ (operation 212). The system may create feature labels and assign class labels (operation 214). The system may then train, validate, and select a model to detect anomalies (operation 216).

The system subsequently monitors the user with the model to detect an impending physiological condition and send one or more recommendations (operation 218). When the system detects that the physiological condition is impending (or that the user currently has a particular physiological condition), the system selects a recommendation and sends the recommendation to the user. For example, the system may predict that the user will have a panic attack within an hour and sends a recommendation to perform breathing exercises. The system may also detect that a user (e.g., software developer) is falling asleep and sends a recommendation to exercise to the user.

The system may account for the user's context, such as the air pollution level, the level of oxygen in the air, or the user's current elevation, to improve the predictions. In some instances, the system may detect environmental changes which trigger the user's symptoms. For example, the system may detect that the smog level or pollen level is high and that the environmental factors will trigger the user's symptoms. The system can also account for the user's activity, such as standing still, walking, running, or mountain climbing. The system may also account for time, season, and other contextual and/or historical data. The system can distinguish between symptoms resulting from a recurrence of the user's health condition (e.g., health disorder) or symptoms due to external factors or the user's activity and send the recommendation as appropriate.

The details for each of the operations are discussed below, along with specific examples from the study.

Collecting Data to Train Models

To obtain data to train models, the inventors sought users who suffered from panic disorder to participate in a data collection study. Ten study participants each received a wearable device, along with instructions to download the corresponding mobile application that the user used to report when panic episodes occurred. The inventors asked the users to wear the device as often as possible for 3 weeks and to use the corresponding mobile application/widget to report when they experienced a panic attack. A widget that resided on the user's mobile phone home screen allowed for easy reporting of panic episodes. Participants tapped the widget to start and stop recording the experience of panic episode symptoms. At the completion of an episode the inventors asked users to rate the severity of symptoms they had just experienced. In total, the inventors asked users to rate the severity of 15 symptoms using a severity rating of 1-5, with 1 being least severe and 5 being most severe.

Figure 3A:
FIG. 3A and FIG. 3B presents a list of symptoms that users from a study reported on after a panic episode subsided.
Figure 3B:

FIG. 3A and FIG. 3B present a list of symptoms 300 that the inventors asked users to report on after a panic episode had subsided, as well as a list 302 of the description for each severity value. The symptoms listed are from the Diagnostic and Statistical Manual of Mental Disorders (DSMIV) and the Panic Disorder Severity Scale standard instrument. The study was approved by Palo Alto Research Center's Institutional Review Board and all users signed informed consent forms.

Figure 4:
FIG. 4 presents a block diagram illustrating an exemplary screenshot of a mobile reporting application, in accordance with an embodiment of the present invention.

FIG. 4 presents a block diagram illustrating an exemplary screenshot 400 of a mobile reporting application, in accordance with an embodiment of the present invention. As depicted in FIG. 4, a user can rate the severity of symptoms and emotions of a panic episode using a mobile recording application executing on a mobile device. The user can indicate levels of anxiety, worry, shortness of breath, racing/pounding heart, dizziness/faintness, and chest pain/discomfort. The user can push on an increase severity button 402 or an decrease severity button 404 to indicate the severity of the symptoms that the user feels. In the illustrated embodiment, a severity level of 4 indicates the severity level is extreme and the severity level of 3 indicates a moderate severity level. A severity level of 1 indicates that the severity level is none.

Dataset Summary

Out of the ten individuals who signed up for the study, five were female, four male and one user identified as transmale. The minimum age was 19 and the maximum was 53. From the initial 10 participants, three users did not log any physiological data. The remaining seven users logged data and four of the seven reported at least one panic episode while wearing the device. In total the system recorded 19 panic episodes with corresponding physiological data and symptom severity information. The minimum number of reports made by any individual that logged data was 1 panic report and the maximum was 12 panic reports made by one individual. On average each panic episode lasted approximately 3 minutes and 40 seconds. In total the inventors collected 623 hours, 42 minutes of physiological data, which required a total storage space of 1.26 GB.

The system used the Zephyr BioPatch™ to collect physiological data from users. The Zephyr BioPatch™ is a wireless wearable device that includes a BioModule and holder which attaches to disposable electrocardiogram (ECG) electrodes. The device allows continuous monitoring of a user's physiological information. Measurements recorded by the device include heart rate, respiration rate, R-R interval, activity levels, posture, as well as the raw ECG waveform and breathing waveform.

Data Measurements

An interactive remote health monitoring system may use the following subset of data measurements for analysis: heart rate, respiration rate, heart rate variability, core temperature and activity. A wearable sensor device samples each measurement at a rate of 1 Hz and the measurements are explained in more detail below.

1. Heart rate. The number of beats per minute of a user's heart.

$$HR = 60/RR \text{ interval}$$

The R-R interval is the time between heart beats, which is determined by the interval between R peaks in the QRS complex from the electrocardiogram signal.

2. Respiration rate. The number of breaths the user takes per minute. A pressure sensor detects torso expansion and contraction due to breathing.

3. Heart rate variability (HRV). HRV is measured by computing the standard deviation of the normal to normal intervals (SDNN). Normal-to-normal intervals are represented by a collection of the past 300 R-R intervals, hence:

$$SDNN = \sqrt{\frac{1}{N}\sum_{i=1}^{N}(RR_i - \widehat{RR})^2}$$

$RR_i$ refers to an individual R-R interval within a rolling window period and $\widehat{RR}$ refers to the average R-R interval value within the rolling window. The Zephyr BioPatch™ uses a value of N=300 for the rolling window.

4. Core temperature. Estimated core body temperature calculated from heart rate data. The Zephyr BioPatch™ calculates and makes available the core temperature.

5. Activity $$VMU(g) = \sqrt{x^2 + y^2 + z^2}$$

The system may measure vector magnitude units in the force of gravity, g. The system may take average values over the previous second for the three axial acceleration magnitudes, (x, y, and z), sampled at 100 Hz. This results in approximate values for activity types, e.g. VMU(g)≈0.2 indicates the user is walking and VMU(g)≈0.8 indicates the user is running.

Panic Episode Prediction—Data Processing

When a user wears a sensor device this results in a session of collected data, which may be stored in comma-separated values (CSV) file format. The system may flag sessions as either containing a panic episode or not containing an episode, based on the user's report of severity of symptoms. In some implementations, the system may label a session as containing a panic episode if the user's feedback regarding panic symptoms exceeds one or more predetermined threshold values. The system may process each session that contains a panic episode by extracting a time-slice surrounding each reported panic episode. In some implementations, the system may set a duration of 71 minutes for a time-slice, which includes time up to 60 minutes prior to the reported episode, the first minute of the episode, and the remaining 10 minutes following the report. If the system does not record a full 60 minutes worth of physiological data before a user reports a panic episode, the system may use less than 71 minutes of data to represent the panic episode.

As the system samples physiological data at a rate of 1 Hz, the system may perform a rollup by computing the average value for each one minute interval. The system may also interpolate any missing values due to sensor drop out. The system may also process sessions with no reported panic episodes by splitting the data into equivalent 71 minute time-slices and performing the same rollup and interpolation operations. This results in a collection of matrices that the system may use to represent each panic or non-panic time-series.

$$E^k = \begin{bmatrix} | & | & | & | & | \\ HR & BR & \text{Activity} & HRV & \text{Temp} \\ | & | & | & | & | \end{bmatrix}$$

$E^k \in \mathfrak{R}^{71 \times 5}$, k=1 . . . N, where N is the total number of episodes.

In total the system constructed 19 panic matrices and 280 non-panic matrices using data collected from the study.

Dealing with Activity

Since the system infers psychological state information from physiological data, the system needs to account for physical activity to ensure that any changes observed in a signal are not merely due to motion artifacts. In order to account for physical activity the system may construct individual regression models for each user from data collected when the user did not experience any panic episodes.

$$y_{HR} = \beta_{0,HR} + \beta_{1,HR} x_{act} + \epsilon_{HR} \quad (1)$$

$$y_{BR} = \beta_{0,BR} + \beta_{1,BR} x_{act} + \epsilon_{BR} \quad (2)$$

$$y_{HRV} = \beta_{0,HRV} + \beta_{1,HRV} x_{act} + \epsilon_{HRV} \quad (3)$$

$$y_{Temp} = \beta_{0,Temp} + \beta_{1,Temp} x_{act} + \epsilon_{Temp} \quad (4)$$

Each y represents the value that would be expected, given that a user was not experiencing panic and the user was exerting a certain amount of physical activity $x_{act}$. The system may create training and test sets using an 80/20 split of the data. In some implementations, the system may choose from a range of transformations (e.g., including $\log(x_{act})$ and $\sqrt{x_{act}}$) for the predictor variable $x_{act}$. The system may select the regression model which maximizes the $R^2$ value on the out-of-sample test set. In some implementations, the system may use an rlm function (e.g., Robust Fitting of Linear Models) from the "Modern Applied Statistics with S" (MASS) package in R to fit individual models for each user using robust regression. Note that R is a software environment for statistical computing and graphics. The system may compute a result that is an expected value for each physiological variable of interest over the range of physical activity from sedentary to active for each user.

Figure 5A:
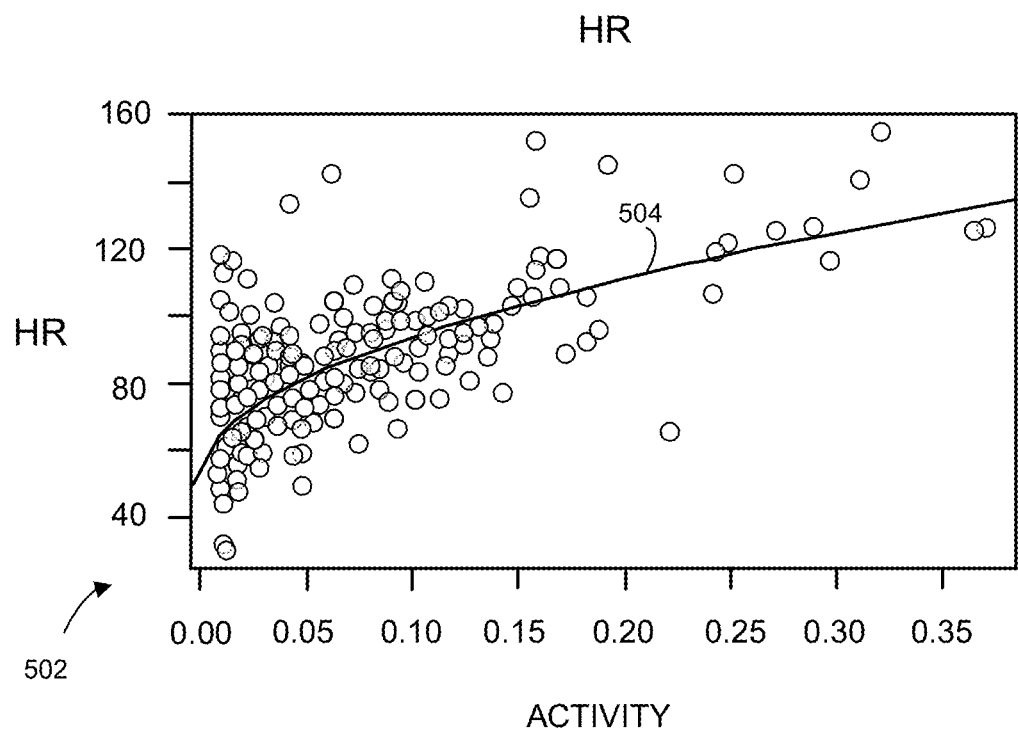
FIG. 5A-FIG. 5D illustrate exemplary scatter plots of physiological response variables and the learned regression models for an individual user from the study.

FIG. 5A-FIG. 5D illustrate exemplary scatter plots of physiological response variables and the learned regression models for an individual user from the study. The values shown in the scatter plots are from the user's test set. FIG. 5A illustrates a scatter plot 502 with heart rate on the vertical axis and activity level on the horizontal axis. The heart rate increases as the activity level increases, and FIG. 5A also includes a plot 504 of the regression model.

Figure 5B:
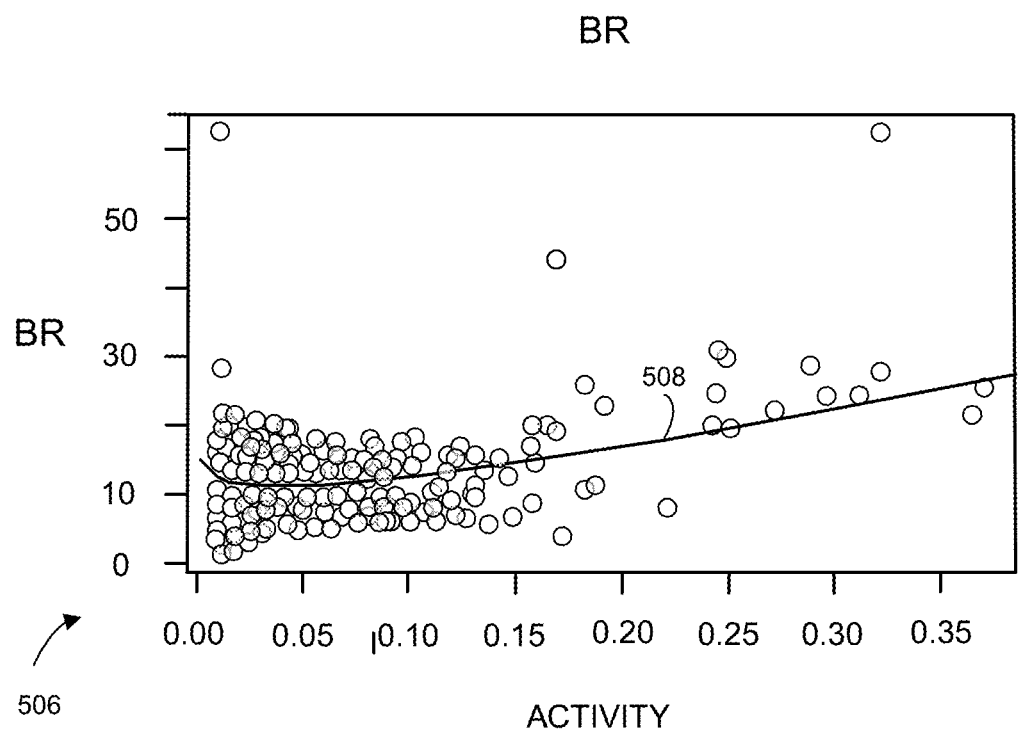

FIG. 5B illustrates a scatter plot 506 with respiration rate on the vertical axis and activity level on the horizontal axis. FIG. 5B also includes a plot 508 of the associated regression model.

Figure 5C:
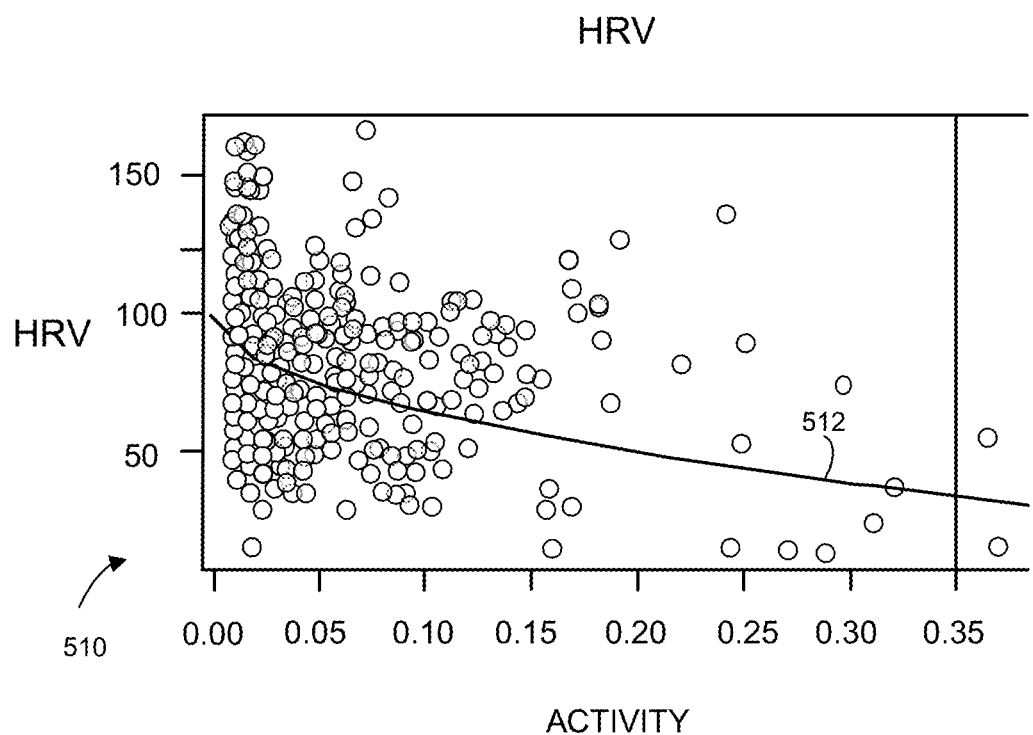

FIG. 5C illustrates a scatter plot 510 with heart rate variability on the vertical axis and activity level on the horizontal axis. FIG. 5C also includes a plot 512 of the associated regression model.

Figure 5D:
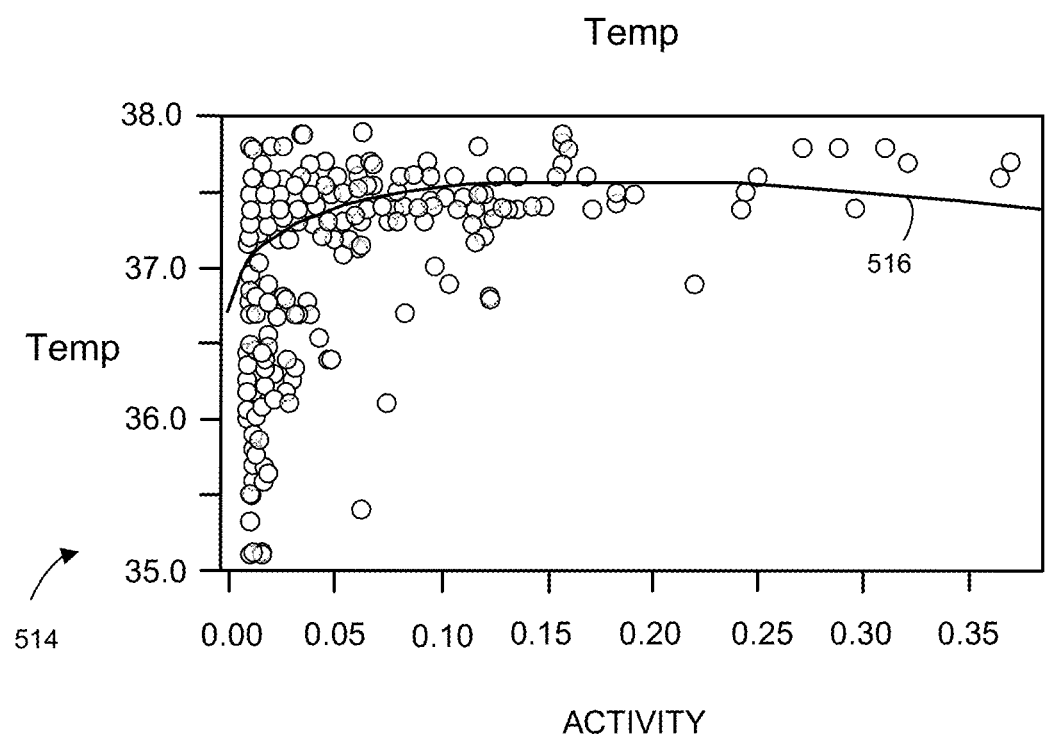

FIG. 5D illustrates a scatter plot 514 with temperature on the vertical axis and activity level on the horizontal axis. FIG. 5D also includes a plot 516 of the associated regression model.

Figure 6:
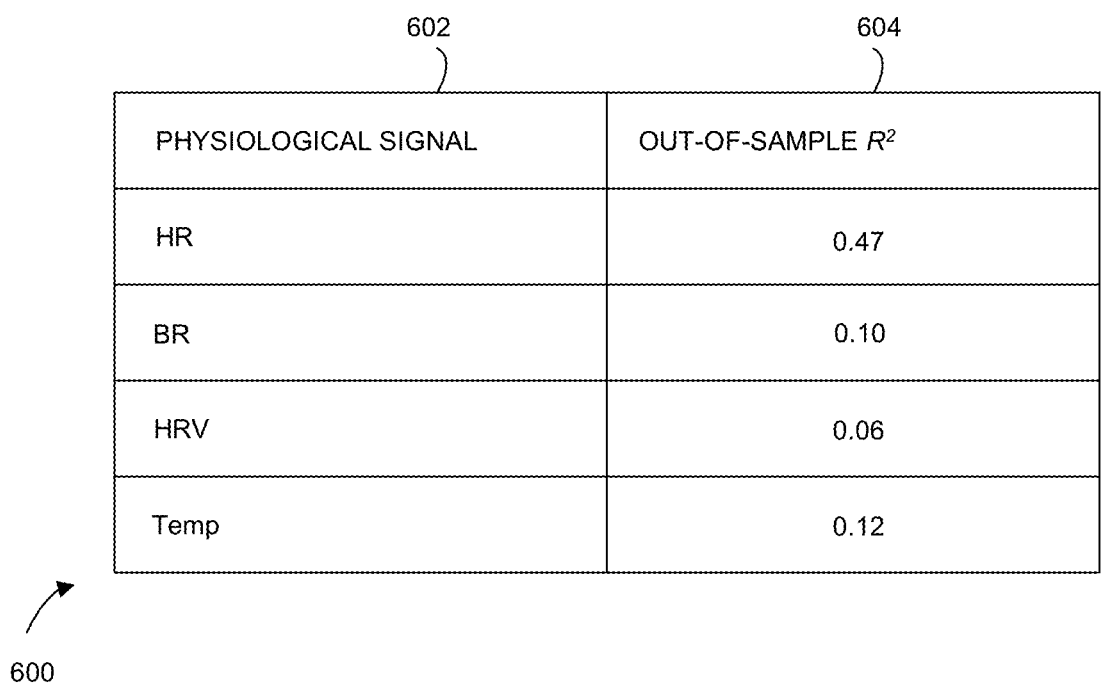
FIG. 6 presents a table illustrating out-of-sample $R^2$ values for each of the regression models.

FIG. 6 presents a table 600 illustrating out-of-sample $R^2$ values for each of the regression models. As illustrated in FIG. 6, a column 602 displays the physiological signal and a column 604 displays the corresponding out-of-sample $R^2$ value. For example, the heart rate physiological signal has out-of-sample $R^2$ value of 0.47.

Given individual regression models for expected non-panic physiological variable measurements, and original values in panic and non-panic episode matrices $E^k$, the system may compute delta matrices $D^k$:

$$D_{i=1\ldots71,HR}^k = y_{HR}^i - E_{i,HR}^k \quad (5)$$

$$D_{i=1\ldots71,BR}^k = y_{BR}^i - E_{i,BR}^k \quad (6)$$

$$D_{i=1\ldots71,HRV}^k = y_{HRV}^i - E_{i,HRV}^k \quad (7)$$

$$D_{i=1\ldots71,Temp}^k = y_{Temp}^i - E_{i,Temp}^k \quad (8)$$

In the above equations, k is the total number of panic and non-panic matrices and $y^i$ is the expected value from the regression model at time i. $D_{i,j}^k$ refers to the (i,j) entry in the delta matrix and HR, BR, HRV, and Temp represent individual columns in the matrix. Each delta matrix $D^k$ represents the difference between the expected value of the physiological signal, given an amount of physical activity $x_{act}$, and the actual physiological value observed.

Change-Point Analysis

Once physical activity has been accounted for and the delta matrices constructed the system may apply change point analysis to detect significant changes within the time-series data of each physiological variable, $D_{i=1\ldots71,HR}^k$, $D_{i=1\ldots71,BR}^k$, $D_{i=1\ldots71,HRV}^k$, $D_{i=1\ldots71,Temp}^k$. The system may perform single change point detection by attempting to locate the time point $t_c$ such that the average value of the outcome variable $u_0$ up to time point $t_c$ is significantly different from the average value of the outcome variable $u_1$ following time point $t_c$.

Figure 7:
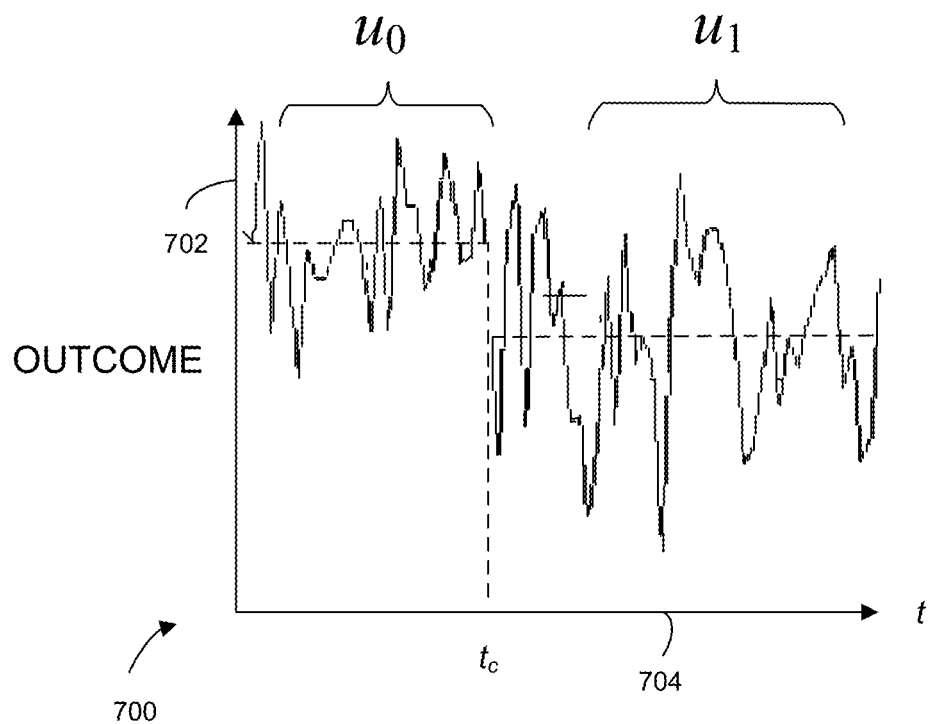
FIG. 7 illustrates an exemplary graph with single change point detection, in accordance with an embodiment of the present invention.

FIG. 7 illustrates an exemplary graph 700 with single change point detection. As depicted in FIG. 7, a vertical axis 702 indicates outcome, while a horizontal axis 704 indicates time, and $t_c$ is the maximum likelihood estimate of a significant change in the distribution of the time-series data.

The system can detect multiple change points within a collection of time-series data by beginning with a segment of data t∈0 . . . a and locating the first change-point (e.g., may choose a minimum change point duration of a=5). If no change point is detected within the segment 0 . . . a, the system may increase a by 1 and repeat the procedure until a change point is found or the entire time-series is evaluated, in which case no change points are found. When the system finds a change point within the segment, the system may repeat the procedure beginning from time point a. The result of applying change-point analysis is that the system may construct change point matrices that concisely capture the location and magnitude of significant change points in time series data.

The system may perform change point analysis on each physiological variable in the delta matrices. As in the study, this may lead to matrices that capture up to an hour's worth of change point information, either preceding a panic episode, or during a non-panic interval $CP(D_{i=1\ldots60,j}^k)$, where j∈{HR, BR, HRV, Temp}.

Figure 8:
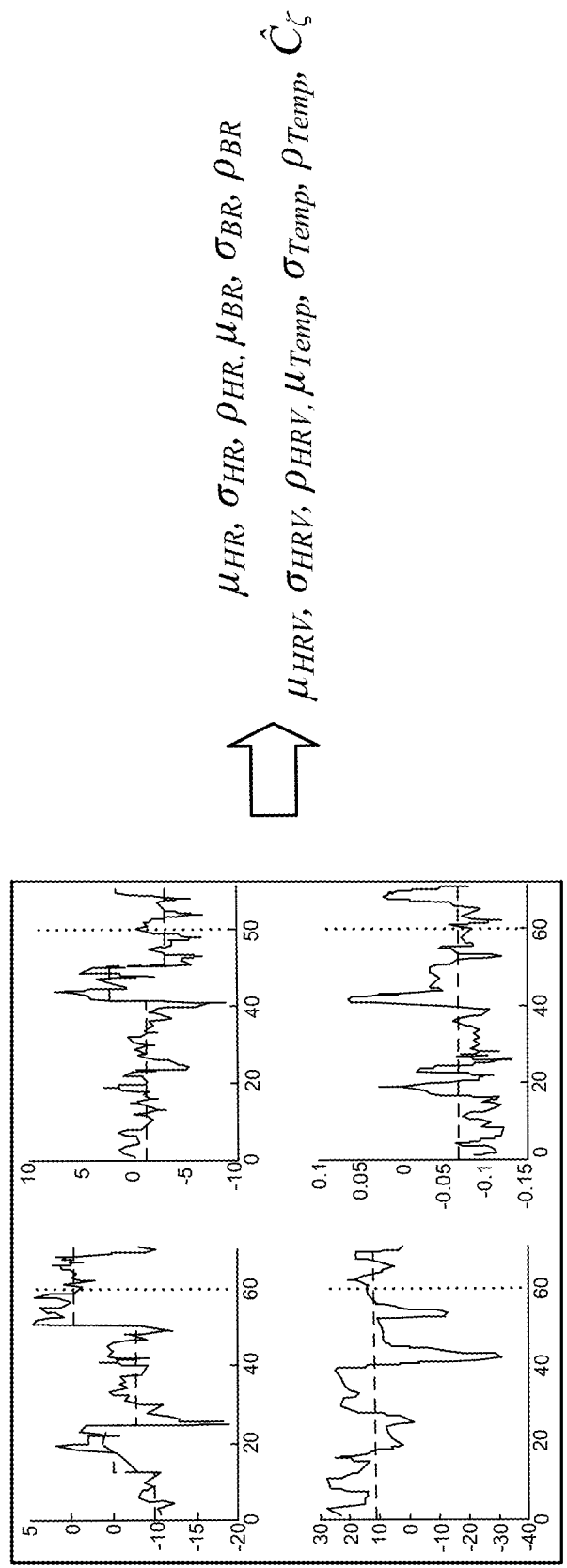
FIG. 8 illustrates generating summary statistics from change point matrices, in accordance with an embodiment of the present invention.

After performing change point detection, the system may generate summary statistics from the change point matrix $CP(D^k)$. FIG. 8 illustrates generating summary statistics from change point matrices. The summary statistics representing each time-series may be as follows:

$\mu_{HR}, \sigma_{HR}, \rho_{HR}, \mu_{BR}, \sigma_{BR}, \rho_{BR}$
$\mu_{HRV}, \sigma_{HRV}, \rho_{HRV}, \mu_{Temp}, \sigma_{Temp}, \rho_{Temp}, \hat{C}_\xi$ The values above capture summary statistics for each measurement type HR, BR, HRV, and Temp, where μ refers to the average value, σ is the standard deviation, ρ refers to the number of change points and $\hat{C}_\xi$ is the average location of where change points occur. For each user, the system may construct feature vectors using combinations of the summary statistics above. The system may assign class labels to each feature vector depending on whether the feature vector captures data for a period preceding a panic attack, or the vector captures data when no panic attack was reported.

Anomaly Detection

There were many more instances of negative class labels (e.g., no panic attack reported) compared to positive class labels (e.g., panic attack reported) in the study. This means that the collected dataset was skewed towards negative instances. The inventors chose to perform anomaly detection instead of standard classification techniques since anomaly detection is suited to handle skewed classes.

Anomaly detection attempts to identify observations within a dataset that do not conform to an expected (e.g., normal) pattern. One can use an unsupervised or supervised learning approach to perform anomaly detection. With labeled data, the system may use a supervised anomaly detection approach with an estimated Gaussian distribution and a collection of normal training examples. After determining a fit for a Gaussian distribution, the system may identify any instance that produced sufficiently low probability values (e.g., less than a threshold ε) as an outlier outside the normal distribution.

Supervised Anomaly Detection Model Selection

Figure 9:
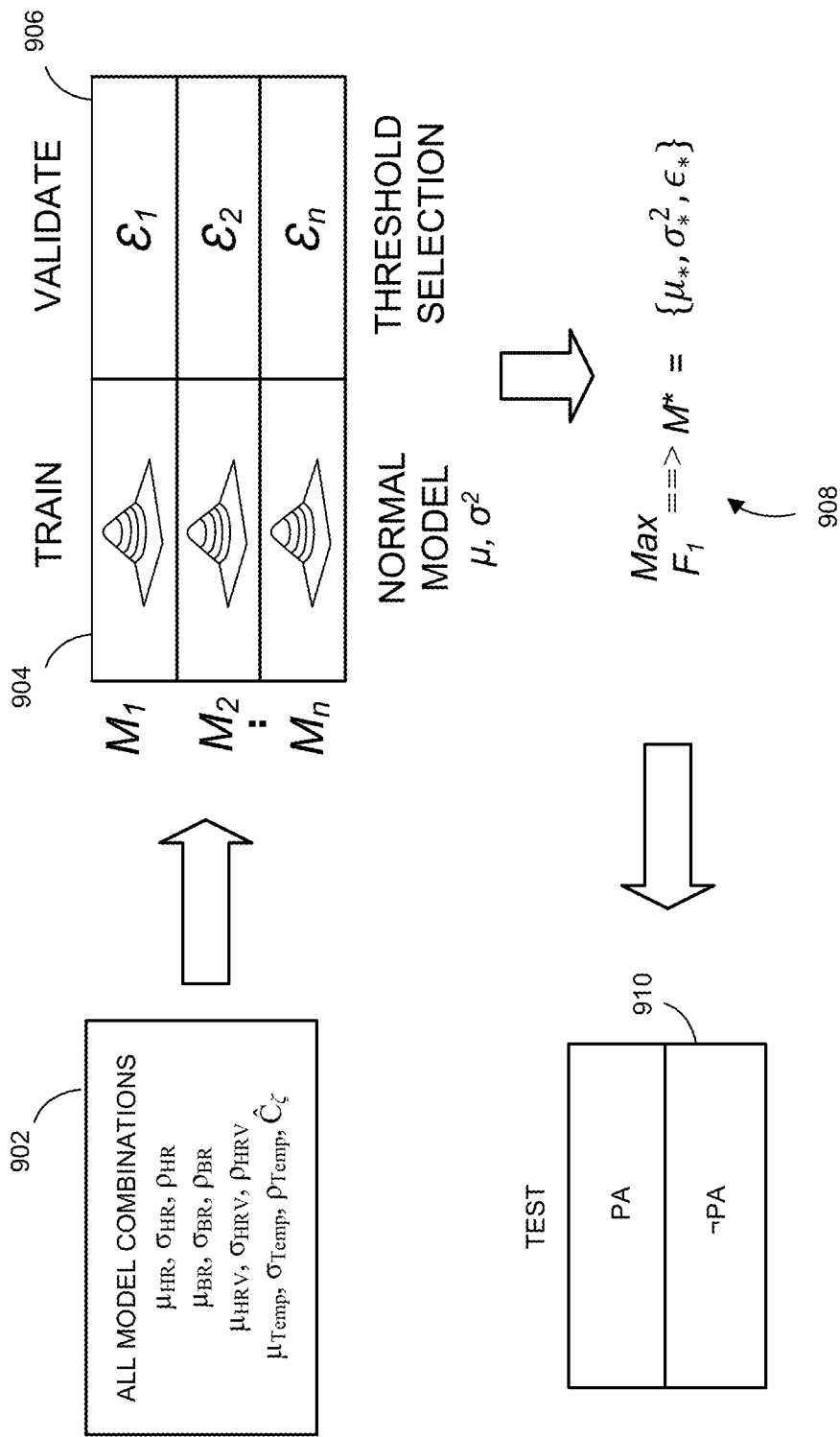
FIG. 9 presents a block diagram illustrating an overview of supervised anomaly detection model selection, in accordance with an embodiment of the present invention.

The system may construct a separate data set for a respective user and may further split the data set into training, validation, and test sets. FIG. 9 depicts a high level overview of a procedure for training models, selecting the threshold parameter, selecting the model, and evaluating the selected model using the training, validation, and test sets.

FIG. 9 presents a block diagram illustrating an overview of selecting a supervised anomaly detection model, according to an embodiment. During operation, the system may initially produce and evaluate a collection of models by enumerating all possible combinations of the summary statistics (operation 902). The system may then construct the normal model using the training dataset (operation 904). The system may use the validation set to select the ϵ parameter (operation 906) and perform model selection (operation 908). Finally, the system may use a held-out test dataset, which includes novel unseen instances, to evaluate the selected model M* (operation 910). Each step is described in more detail below.

Normal Model

The system may learn a normal model by estimating the parameters of a Gaussian distribution using the training dataset. The system may use maximum likelihood estimation to determine mean and variance parameters for the Gaussian distribution:

$$\mu = \frac{1}{m}\sum_{i=1}^{m} x^{(i)}$$

$$\sigma^2 = \frac{1}{m}\sum_{i=1}^{m} (x^{(i)} - \mu)^2$$

The system may estimate mean and variance parameters for each variable included in the model, $\mu \in R^n$ and construct a covariance matrix $\Sigma \in R^{n \times n}$ where the diagonal entries are the values of $\sigma^2$ and off-diagonal entries are zero. The system may then use these parameters to compute the probability density function of the multivariate Gaussian distribution:

$$p(x; \mu; \Sigma) = \frac{1}{\sqrt{(2\pi)^n |\Sigma|}} \exp\left(-\frac{1}{2}(x-\mu)^T \Sigma^{-1}(x-\mu)\right)$$

After determining the probability density function, new instances x are considered to be outliers if $p(x; \mu; \Sigma) < \epsilon$. In this case the system may label the new instance as an approaching panic episode. If $p(x; u; \Sigma) > \epsilon$, then the system may label the new instance as not an approaching panic episode.

Threshold Selection

The system may select the parameter ϵ using the validation set. First, the system determines values for $p(x; \mu; \Sigma)$ for all instances within the validation set. The system then selects the parameter ϵ by evaluating the accuracy of predictions. The system may step through min(p) to max(p) and choose the ϵ which maximizes the $F_1$ score on validation set data. The $F_1$ score is the harmonic mean, given by $$F_1 = \frac{2 \cdot P \cdot R}{P + R},$$

where P is precision and R is recall.

In the case where the validation set contains no positive instances, it does not make sense to optimize the $F_1$ measure as this would result in no true positives. Instead, for this case, the system may select the value of ϵ as min(p).

Model Selection

In addition to parameter selection and determining the normal model, the system may also use the training and validation set to perform automatic model selection. The system can select a model by considering all combinations of the 13 summary statistics described above. In total, the system may evaluate $2^{13}-1$ models on the training and validation data. The system may select the model M* which maximizes the $F_1$ score for evaluation using the held-out test set.

Study Results

Below is a description of the precision and recall results for each of the seven users that recorded physiological data for the study. The system constructed individual models for each user. Four of the users reported panic episodes while wearing the device. The analysis below includes all panic episodes that had at least 15 minutes of physiological data preceding the report. This requirement led to two of the panic episodes being removed from the analysis. Three of the users collected physiological data, but either did not report any panic episodes, or reported an episode when they were not wearing the device. FIG. 10 presents a table 1000 illustrating the total number of non-panic and panic instances included in the analysis for each user. From the total instances in FIG. 10, the system constructed training, validation and held-out test sets as follows:

Training set: the system used 80% of the non-panic (e.g., normal) episodes to construct a normal model.

Validation set: the system included 50% of reported panic episodes in the validation set. The system combined the training and validation set to perform threshold (ϵ) selection. In the case where no panic episodes were reported, the system used the training set by itself to perform threshold selection.

Held out test set: The system held out the remaining 20% of non-panic episodes and 50% of panic episodes to evaluate the learned model.

Where it was possible, the system performed two separate runs in which the system swapped 50% of reported panic episodes between the validation and test set. This allowed all panic episodes a chance to be evaluated by including them in the held-out test set, while still training models on separate training validation data. The total sum of classifications made by the two runs are reported.

The description below presents for each user a confusion matrix, as well as the precision, recall, and $F_1$ score. The rows of the confusion matrix are the predictions of the model and the columns are the actual outcomes. The diagonal entries of the confusion matrix capture the number of panic and non-panic episodes that the disclosed technique correctly labeled in the test-set, i.e. the true positives and true negatives. The off-diagonal entries capture the number of incorrectly labeled episodes in the test-set inferred by the technique, i.e. false positives and false negatives. For each user, the description below also reports the automatically selected model M*. The description reports a single M* for each user as, in each case, the system selected the same M* during both runs of the disclosed process.

Figure 11:
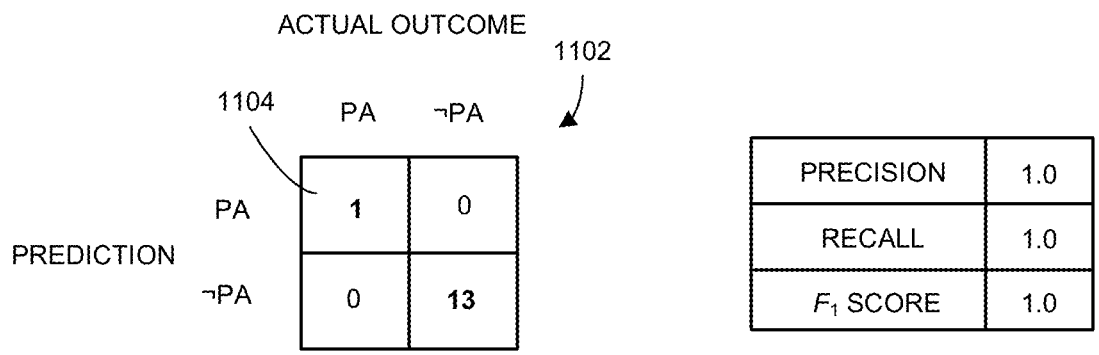
FIG. 11 illustrates a confusion matrix and precision/recall results for User 1.

FIG. 11 illustrates a confusion matrix 1102 and precision/recall results for User 1. Confusion matrix 1102 shows that the system correctly labeled all of the test-set instances. User 1 reported only one panic episode, which the system correctly classified (e.g., top left box 1104). The system generated no false positives or false negatives, giving 100% precision and recall for User 1. The automatically selected model was:

$$M^*=\{\mu_{BR}\}$$

Figure 12:
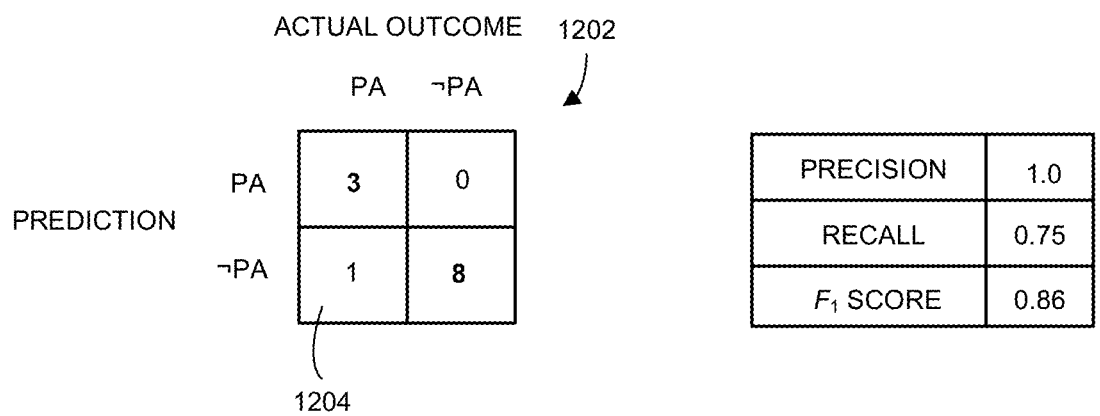
FIG. 12 illustrates a confusion matrix and presentation/recall results for User 2.

FIG. 12 illustrates a confusion matrix 1202 and presentation/recall results for User 2. The confusion matrix shows that the system correctly labeled all but one (e.g., bottom left box 1204) of the test-set instances. The system had 100% precision, and generated no false positives for User 2. The system incorrectly labeled one of the panic episodes as non-panic, giving a recall score of 75%. The selected model for User 2 was the number of change points in the breathing rate and temperature measurements:

$$M^*=\{\rho_{BR},\rho_{Temp}\}$$

Figure 13:
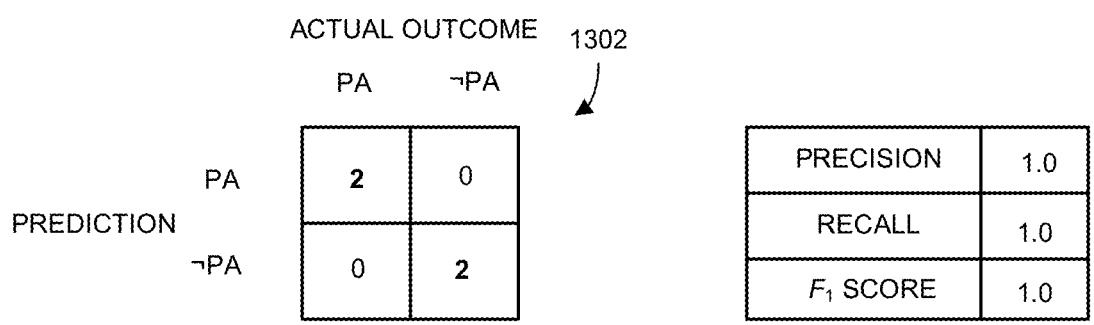
FIG. 13 illustrates a confusion matrix and precision/recall results for User 3.

FIG. 13 illustrates a confusion matrix 1302 and precision/recall results for User 3. While the size of the dataset collected for User 3 was limited, the results show that the disclosed approach correctly classified all panic and non-panic episodes in the test-set, giving a value of 100% for precision, recall and the $F_1$ score. For User 3, the model that the anomaly detection procedure automatically chose included only the average heart rate:

$$M^*=\{\mu_{HR}\}$$

Figures 14, 15:
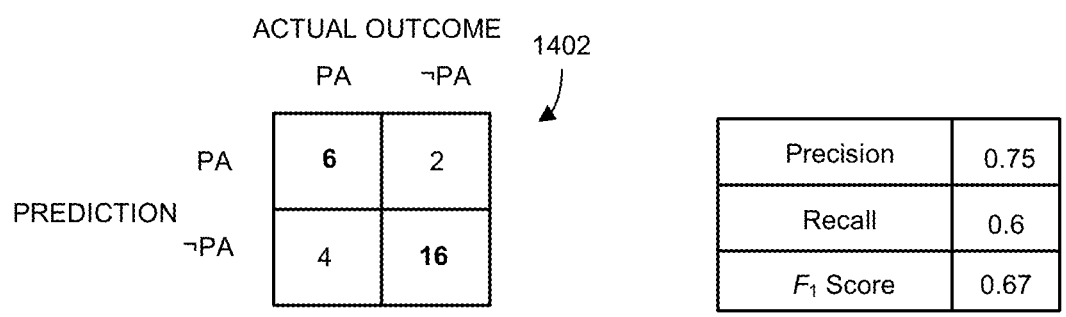
FIG. 14 illustrates a confusion matrix and presentation/recall results for User 4.
FIG. 15 presents the macro results for all four users who reported panic episodes.

FIG. 14 illustrates a confusion matrix 1402 and presentation/recall results for User 4. User 4 had the highest number of positive instances in the dataset. Overall, the system correctly labeled 6 panic episodes and had two false positives, giving a precision of 75%. The system misclassified the remaining 4 panic episodes as non-panic episodes giving a recall rate of 60%. The overall $F_1$ score for User 4 was 67%. The model that the system selected for User 4 included the number of change points in the heart rate, temperature measurements, the average breathing rate, and heart rate variability:

$$M^*=\{\rho_{HR},\mu_{BR},\mu_{HRV},\rho_{Temp}\}$$

FIG. 15 presents the macro results for all four users who reported panic episodes. Overall, the disclosed approach for predicting panic attacks from physiological input variables achieved 93.8% precision and 83.8% recall. This produced a macro harmonic mean score of 88.5%.

FIG. 16 illustrates the confusion matrix results 1602, 1604, and 1606 for Users 5, 6 and 7, respectively. FIG. 16 displays results for the three users who recorded physiological data, but did not report any panic attacks while wearing the device. In both runs for User 5, the system incorrectly labeled one instance as a panic episode, giving a total of two false positives. The system correctly labeled all other instances for User 5 as non-panic episodes. For Users 6 and 7, the system correctly labeled all instances in the test-set as non-panic episodes.

Figure 17:
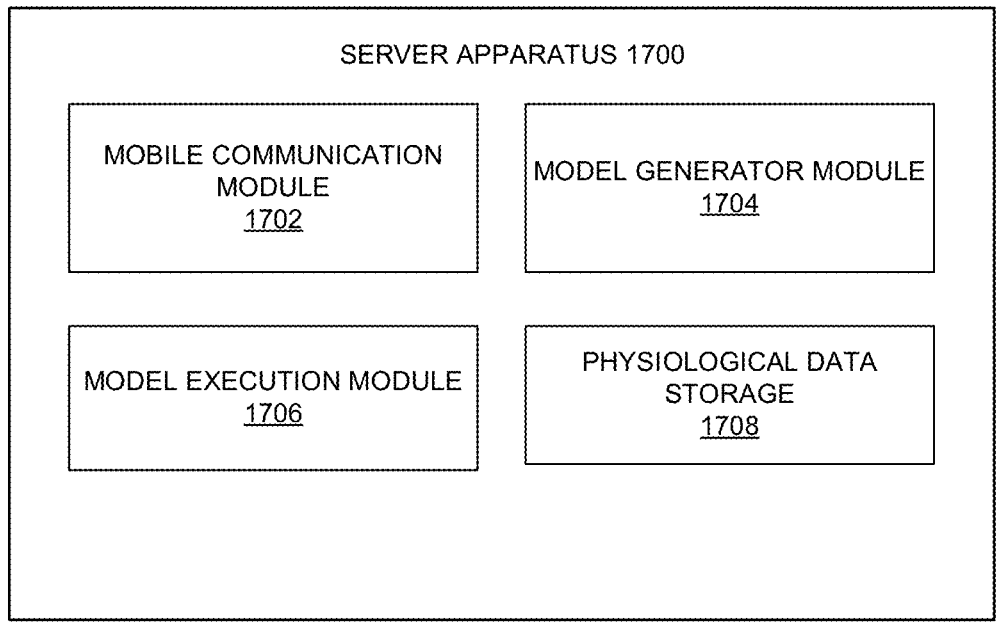
FIG. 17 illustrates an exemplary server apparatus, in accordance with an embodiment.

FIG. 17 illustrates an exemplary server apparatus 1700 that facilitates interactive remote health monitoring, in accordance with an embodiment. Apparatus 1700 can comprise a plurality of modules which may communicate with one another via a wired or wireless communication channel. Apparatus 1700 may be realized using one or more integrated circuits, and may include fewer or more modules than those shown in FIG. 17. Further, apparatus 1700 may be integrated in a computer system, or realized as a separate device which is capable of communicating with other computer systems and/or devices. Specifically, apparatus 1700 can comprise a mobile communication module 1702, a model generator module 1704, a model execution module 1706, and a physiological data storage 1708.

Mobile communication module 1702 receives physiological data from a mobile device and sends recommendations to the mobile device. Model generator module 1704 generates a prediction model for a user based on physiological data associated with the user and activity data. Model execution module 1706 uses the generated model to analyze the user's physiological data and contextual data to predict panic attacks. Physiological data storage 1708 stores physiological data for the user.

Exemplary Mobile Device

Figure 18:
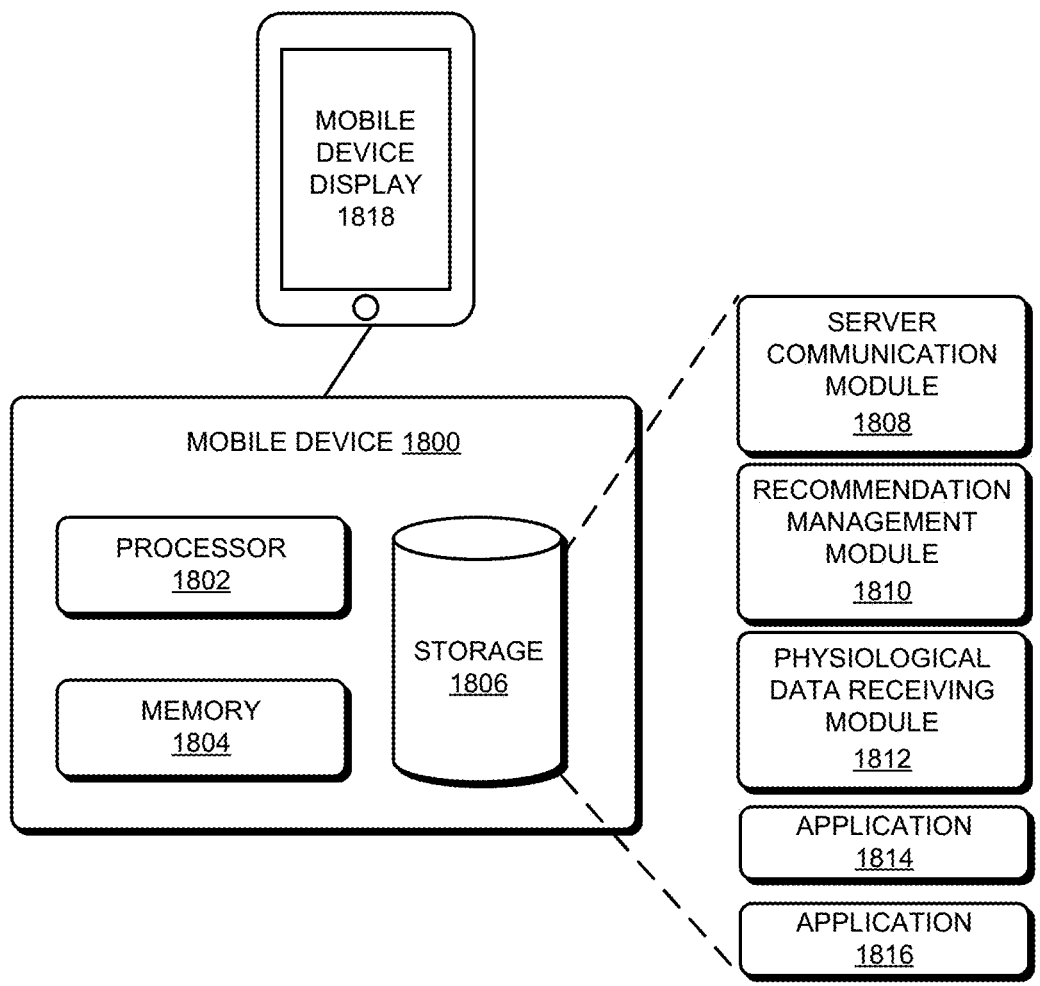
FIG. 18 presents an exemplary mobile device, in accordance with an embodiment of the present invention.

FIG. 18 presents an exemplary mobile device 1800 in an interactive remote health monitoring system, in accordance with an embodiment of the present invention. In FIG. 18, mobile device 1800 includes a processor 1802, a memory 1804, and a storage device 1806. Storage device 1806 stores programs to be executed by processor 1802. Specifically, storage device 1806 stores a server communication module 1808, a recommendation management module 1810, and a physiological data receiving module 1812, as well as other applications, such as applications 1814 and 1816.

Server communication module 1808 may send physiological data to a server. Recommendation management module 1810 receives recommendations from a server and displays the recommendations to a user on a mobile device display 1818. Recommendation management module 1810 may display a message and/or read the message to a user. Recommendation management module 1818 may also receive user feedback regarding the recommendations and user symptoms, and server communication module 1808 may send the feedback to the server. Physiological data receiving module 1812 receives the physiological data from a wearable device.

During operation, server communication module 1808, recommendation management module 1810, and physiological data receiving module 1812 are loaded from storage device 1806 into memory 1804 and then executed by processor 1802. While executing the program, processor 1802 performs the aforementioned functions.

Figure 19:
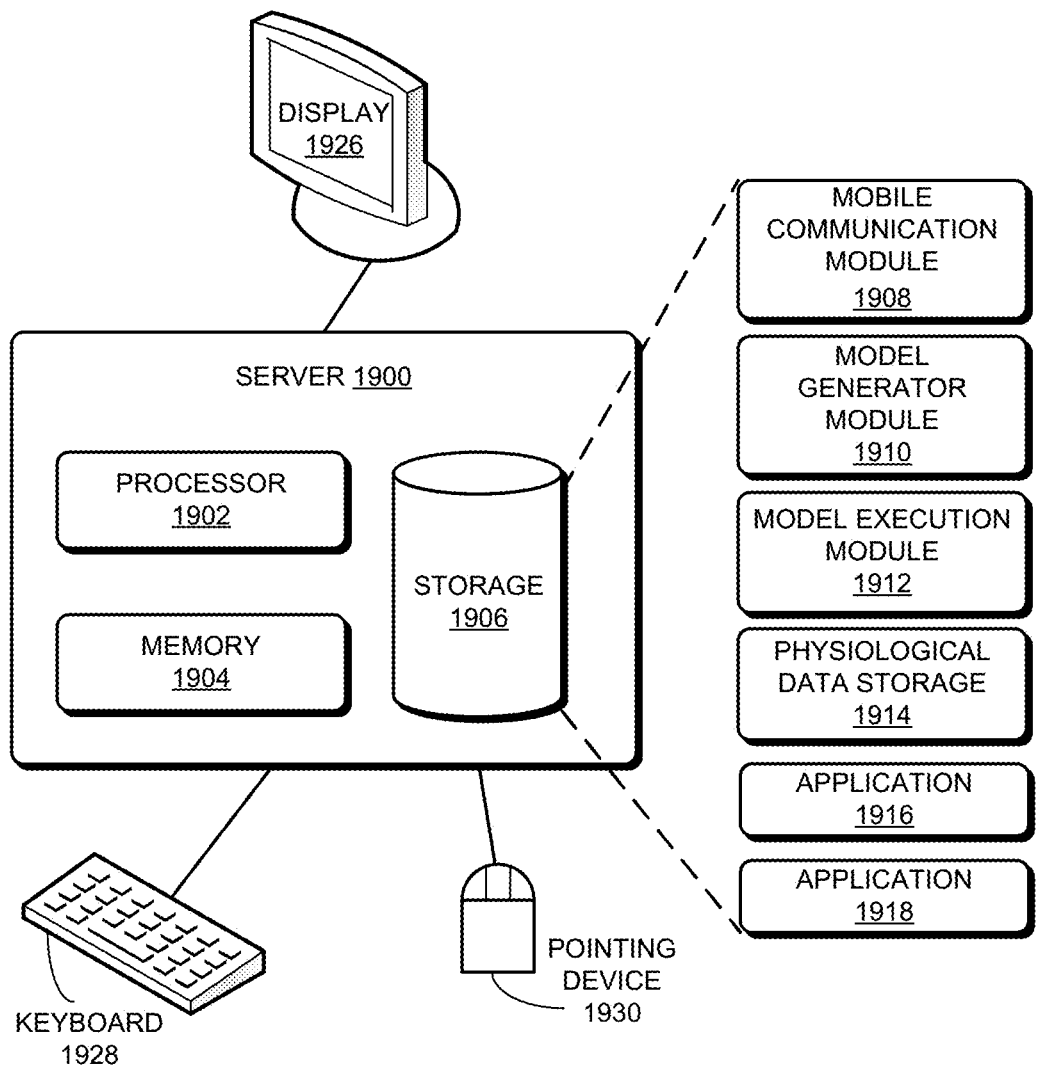
FIG. 19 presents an exemplary server in an interactive remote health monitoring system, in accordance with an embodiment of the present invention.

FIG. 19 presents an exemplary server 1900 in an interactive remote health monitoring system, in accordance with an embodiment of the present invention. In FIG. 19, server 1900 includes a processor 1902, a memory 1904, and a storage device 1906. Storage device 1906 stores programs to be executed by processor 1902. Specifically, storage device 1906 stores a mobile communication module 1908, a model generator module 1910, a model execution module 1912, and a physiological data storage 1914, as well as other applications, such as applications 1916 and 1918.

Mobile communication module 1908 receives physiological data from a mobile device and sends recommendations to the mobile device. Model generator module 1910 generates a prediction model for a user based on physiological data associated with the user and activity data. Model execution module 1912 uses the generated model to analyze the user's physiological data and contextual data to predict panic attacks. Physiological data storage 1914 stores physiological data for the user. During operation, mobile communication module 1908, model generator module 1910, model execution module 1912, and physiological data storage 1914 are loaded from storage device 1906 into memory 1904 and then executed by processor 1902. While executing the program, processor 1902 performs the aforementioned functions. Server 1900 is coupled to an optional display 1926, a keyboard 1928, and a pointing device 1930.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A computer-executable method for generating a personalized health management recommendation for a user, comprising:
    obtaining sample physiological data, generated by a wearable device worn by the user, that indicates a physiological condition of the user;
    obtaining sample contextual data associated with environmental conditions surrounding the user;
    generating a model for the user based on the sample physiological data and the sample contextual data, wherein the model is trained to predict whether the user will experience an upcoming health condition,
    wherein the model is further trained to predict that the user is likely to experience a panic attack within one hour, and
    wherein generating the model further comprises generating at least one regression model for the user based on second physiological data obtained while the user is both performing physical activities and reports a severity of symptoms which are not flagged as a panic attack;
    obtaining real-time physiological data generated by the wearable device;
    obtaining real-time contextual data associated with environmental conditions surrounding the user,
    wherein the sample contextual data and the real-time contextual data are obtained from a remote sensor other than the wearable device or a source other than the wearable device;
    generating a prediction of whether the user will experience the upcoming health condition by using the real-time physiological data and the real-time contextual data as inputs to the trained model;
    sending, to a mobile device associated with the user based on the prediction, an actionable message which indicates to the user the upcoming health condition and which includes information to alleviate the upcoming health condition indicated in the actionable message;
    in response to receiving the actionable message, performing, by the user, an action based on the included information to alleviate the upcoming health condition indicated in the actionable message,
    wherein when the information includes exercise therapy, the action includes performing an exercise routine,
    wherein when the information includes breathing and relaxation exercise instructions, the action includes following the breathing and relaxation exercise instructions using a biofeedback mobile application on the user's mobile device,
    wherein when the information includes musical therapy, the action includes playing a preselected musical playlist on the user's mobile device, and
    wherein when the information includes social therapy, the action includes the user changing a physical environment of the user or seeking out a friend, a family member, or a colleague with whom to speak;
    receiving, from the user, real-time feedback regarding the action performed by the user in response to the information included in the actionable message;
    training the model by updating the model based on the received real-time user feedback regarding the action performed by the user in response to the information included in the actionable message; and
    improving the trained model based on reports from the user, wherein the reports are based on the real-time user feedback.

2. The method of claim 1, wherein generating the model further comprises:
    generating panic matrices and non-panic matrices from the sample physiological data; and
    generating one or more delta matrices using the at least one regression model and the panic matrices and non-panic matrices, wherein a delta matrix represents a difference between expected values of physiological data with an amount of physical activity and actual physiological values observed.

3. The method of claim 1, further comprising determining a change point within a respective time-series data of each physiological variable to generate change point matrices.

4. The method of claim 3, further comprising generating, based on at least one change point matrix, summary statistics that include at least a mean, a standard deviation, and a number of change points for each physiological measurement type obtained from the wearable device.

5. The method of claim 1,
    wherein the real-time contextual data indicates a current context for the user, and wherein the model is further trained based on the real-time contextual data, thereby improving an accuracy of the generated prediction.

6. A non-transitory computer-readable storage medium storing instructions which when executed by a computer cause the computer to perform a method, the method comprising:
    obtaining sample physiological data, generated by a wearable device worn by the user, that indicates a physiological condition of the user;
    obtaining sample contextual data associated with environmental conditions surrounding the user;
    generating a model for the user based on the sample physiological data and the sample contextual data, wherein the model is trained to predict whether the user will experience an upcoming health condition,
    wherein the model is further trained to predict that the user is likely to experience a panic attack within one hour, and
    wherein generating the model further comprises generating at least one regression model for the user based on second physiological data obtained while the user is both performing physical activities and reports a severity of symptoms which are not flagged as a panic attack;
    obtaining real-time physiological data generated by the wearable device;

obtaining real-time contextual data associated with environmental conditions surrounding the user, wherein the sample contextual data and the real-time contextual data are obtained from a remote sensor other than the wearable device or a source other than the wearable device;

generating a prediction of whether the user will experience the upcoming health condition by using the real-time physiological data and the real-time contextual data as inputs to the trained model;

sending, to a mobile device associated with the user based on the prediction, an actionable message which indicates to the user the upcoming health condition and which includes information to alleviate the upcoming health condition indicated in the actionable message;

in response to receiving the actionable message, performing, by the user, an action based on the included information to alleviate the upcoming health condition indicated in the actionable message, wherein when the information includes exercise therapy, the action includes performing an exercise routine, wherein when the information includes breathing and relaxation exercise instructions, the action includes following the breathing and relaxation exercise instructions using a biofeedback mobile application on the user's mobile device, wherein when the information includes musical therapy, the action includes playing a preselected musical playlist on the user's mobile device, and wherein when the information includes social therapy, the action includes the user changing a physical environment of the user or seeking out a friend, a family member, or a colleague with whom to speak;

receiving, from the user, real-time feedback regarding the action performed by the user in response to the information included in the actionable message;

training the model by updating the model based on the received real-time user feedback regarding the action performed by the user in response to the information included in the actionable message; and improving the trained model based on reports from the user, wherein the reports are based on the real-time user feedback.

7. The storage medium of claim 6, wherein generating the model further comprises:

generating panic matrices and non-panic matrices from the sample physiological data; and generating one or more delta matrices using the at least one regression model and the panic matrices and non-panic matrices, wherein a delta matrix represents a difference between expected values of physiological data with an amount of physical activity and actual physiological values observed.

8. The storage medium of claim 6, further comprising determining a change point within a respective time-series data of each physiological variable to generate change point matrices.

9. The storage medium of claim 8, further comprising generating, based on at least one change point matrix, summary statistics that include at least a mean, a standard deviation, and a number of change points for each physiological measurement type obtained from the wearable device.

10. The storage medium of claim 6,
wherein the real-time contextual data indicates a current context for the user, and wherein the model is further trained based on the real-time contextual data, thereby improving an accuracy of the generated prediction.

11. A computing system comprising:
one or more processors;
a memory; and
a non-transitory computer-readable medium coupled to the one or more processors storing instructions stored that, when executed by the one or more processors, cause the computing system to perform a method comprising:

obtaining sample physiological data, generated by a wearable device worn by the user, that indicates a physiological condition of the user;

obtaining sample contextual data associated with environmental conditions surrounding the user;

generating a model for the user based on the sample physiological data and the sample contextual data, wherein the model is trained to predict whether the user will experience an upcoming health condition, wherein the model is further trained to predict that the user is likely to experience a panic attack within one hour, and wherein generating the model further comprises generating at least one regression model for the user based on second physiological data obtained while the user is both performing physical activities and reports a severity of symptoms which are not flagged as a panic attack;

obtaining real-time physiological data generated by the wearable device;

obtaining real-time contextual data associated with environmental conditions surrounding the user, wherein the sample contextual data and the real-time contextual data are obtained from a remote sensor other than the wearable device or a source other than the wearable device;

generating a prediction of whether the user will experience the upcoming health condition by using the real-time physiological data and the real-time contextual data as inputs to the trained model;

sending, to a mobile device associated with the user based on the prediction, an actionable message which indicates to the user the upcoming health condition and which includes information to alleviate the upcoming health condition indicated in the actionable message;

in response to receiving the actionable message, performing, by the user, an action based on the included information to alleviate the upcoming health condition indicated in the actionable message, wherein when the information includes exercise therapy, the action includes performing an exercise routine, wherein when the information includes breathing and relaxation exercise instructions, the action includes following the breathing and relaxation exercise instructions using a biofeedback mobile application on the user's mobile device, wherein when the information includes musical therapy, the action includes playing a preselected musical playlist on the user's mobile device, and wherein when the information includes social therapy, the action includes the user changing a physical environment of the user or seeking out a friend, a family member, or a colleague with whom to speak;

receiving, from the user, real-time feedback regarding the action performed by the user in response to the information included in the actionable message;

training the model by updating the model based on the received real-time user feedback regarding the action performed by the user in response to the information included in the actionable message; and improving the trained model based on reports from the user, wherein the reports are based on the real-time user feedback.

12. The computing system of claim 11, wherein generating the model further comprises:

generating panic matrices and non-panic matrices from the sample physiological data; and generating one or more delta matrices using the at least one regression model and the panic matrices and non-panic matrices, wherein a delta matrix represents a difference between expected values of physiological data with an amount of physical activity and actual physiological values observed.

13. The computing system of claim 12, further comprising determining a change point within a respective time-series data of each physiological variable to generate change point matrices.

14. The computing system of claim 11, further comprising:

wherein the real-time contextual data indicates a current context for the user, and wherein the model is further trained based on the real-time contextual data, thereby improving an accuracy of the generated prediction.

15. The method of claim 1, wherein the actionable message further includes a command instructing the mobile device to play a preselected musical playlist on the mobile device, and wherein in response to receiving the actionable message, the method further comprises playing, by the mobile device, the preselected musical playlist, thereby alleviating the upcoming health condition of the user.

16. The method of claim 1, wherein obtaining the sample physiological data and obtaining the sample contextual data comprises receiving, by a server, the sample physiological data and the sample contextual data, wherein generating the model based on the sample physiological data and the sample contextual data is performed by the server, wherein generating the model for the user based on the sample physiological data and the sample contextual data is performed by the server, wherein obtaining the real-time physiological data and obtaining the real-time contextual data comprises receiving, by the server, the real-time physiological data and the real-time contextual data, and wherein generating the prediction, sending the actionable message, receiving the user feedback, training the model by updating the model, and improving the trained model are performed by the server.

17. The method of claim 1, further comprising:

sending a recommendation to a second mobile device associated with a second user, wherein the recommendation includes information on how to assist or coach the user;

receiving, by the second mobile device of the user, the recommendation, using, by the second user, the information included in the received recommendation to monitor or assist the user, thereby alleviating the upcoming health condition of the user.

18. The method of claim 17, wherein the second user is one or more of:

a medical provider;

a nurse;

a parent; and a coach.

19. The method of claim 1, further comprising:

detecting, based on the trained model, that the user is sleepy;

sending, to the mobile device associated with the user, a recommendation which includes instructions to exercise; and taking, by the user, a break by stopping a current physical activity of the user and performing the instructions in the recommendation.

* * * * *